(12) United States Patent
Poulose et al.

(10) Patent No.: US 7,306,937 B2
(45) Date of Patent: Dec. 11, 2007

(54) MULTIPLY-SUBSTITUTED PROTEASE VARIANTS

(75) Inventors: Ayrookaran J. Poulose, Belmont, CA (US); David A Estell, San Mateo, CA (US); James T Kellis, Jr., Protola Valley, CA (US); Richard R. Bott, Burlingame, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 10/500,943

(22) PCT Filed: Jan. 16, 2003

(86) PCT No.: PCT/US03/01448

§ 371 (c)(1),
(2), (4) Date: Apr. 20, 2005

(87) PCT Pub. No.: WO03/062381

PCT Pub. Date: Jul. 31, 2003

(65) Prior Publication Data

US 2005/0221461 A1     Oct. 6, 2005

(51) Int. Cl.
| | |
|---|---|
| C12N 9/52 | (2006.01) |
| C12N 9/54 | (2006.01) |
| C12N 15/57 | (2006.01) |
| C12N 15/74 | (2006.01) |
| C11D 3/386 | (2006.01) |

(52) U.S. Cl. ............... 435/219; 435/220; 435/221; 435/252.3; 435/320.1; 510/300

(58) Field of Classification Search ............... None
See application file for complete search history.

(56) References Cited

U.S. PATENT DOCUMENTS

| | | | | | |
|---|---|---|---|---|---|
| 5,336,611 | A | * | 8/1994 | van Eekelen et al. | 435/221 |
| 5,352,603 | A | * | 10/1994 | Vetter et al. | 435/221 |
| 5,453,372 | A | * | 9/1995 | Vetter et al. | 435/222 |
| 5,665,587 | A | * | 9/1997 | Aaslyng et al. | 435/221 |
| 5,972,682 | A | * | 10/1999 | Bott et al. | 435/221 |
| 6,287,841 | B1 | * | 9/2001 | Mulleners et al. | 435/221 |
| 6,300,116 | B1 | * | 10/2001 | von der Osten et al. | 435/220 |
| 6,312,936 | B1 | * | 11/2001 | Poulose et al. | 435/219 |
| 6,376,450 | B1 | * | 4/2002 | Ghosh et al. | 510/392 |

(Continued)

FOREIGN PATENT DOCUMENTS

WO    WO 99/20723 A2 *  4/1999

*Primary Examiner*—Nahsaat T. Nashed
*Assistant Examiner*—William W. Moore
(74) *Attorney, Agent, or Firm*—Kamrin T. MacKnight

(57) ABSTRACT

Novel enzyme variants including protease variants derived from the DNA sequences of naturally-occurring or recombinant non-human proteases are disclosed. The variant proteases, in general, are obtained by in vitro modification of a precursor DNA sequence encoding the naturally-occurring or recombinant protease to generate the substitution of a plurality of amino acid residues in the amino acid sequence of a precursor protease. Such variant proteases have properties which are different from those of the precursor protease, such as altered wash performance. The substituted amino acid residue correspond to positions 27, 45, 170, 181, 251 and 271 of *Bacillus amyloliquefaciens* subtilisin. Additional variants comprising at least one additional substitution at a position selected from 1, 14, 49, 61, 87, 100, 102, 118, 128, 204 and 258 of *Bacillus amyloliquefaciens* subtilisin are also described.

7 Claims, 8 Drawing Sheets

```
                                    250  Gln                                          260
       Gln Val Arg Ser Ser Leu Glu Asn Thr Thr Thr Lys Leu Gly Asp Ser Phe Tyr Tyr Gly Lys Gly Leu Ile Asn
1149   CAA GTC CGC AGC AGT TTA GAA AAC ACC ACT ACA AAA CTT GGT GAT TCT TTC TAC TAT GGA AAA GGG CTG ATC AAC 270             275
       Val Gln Ala Ala Ala Gln OC                    TERM
1224   GTA CAG GCG GCA GCT CAG TAA AACATAAAAAACCGGCCTTGGCCCCGCCGGTTTTTATTTTTCTTCCTCCGCATGTTCAATCCGCTCC

1316   ATAATCGACGGATGGCTCCCTCTGAAAATTTTAACGAGAAACGGCGGGTTGACCCGGCTCAGTCCCGTAACGGCCAAGTCCTGAAACGTCTCAATCGCCG

1416   CTTCCCGGTTTCCGGTCAGCTCAATGCCGTAACGGTCGGCGGCGTTTTCCTGATACCGGGAGACGGCATTCGTAATCGGATC
```

U.S. PATENT DOCUMENTS

| | | | |
|---|---|---|---|
| 6,482,628 B1 * | 11/2002 | Poulose et al. | 435/221 |
| 6,599,730 B1 * | 7/2003 | Brode et al. | 435/221 |
| 6,605,458 B1 * | 8/2003 | Hansen et al. | 435/220 |
| 6,610,642 B2 * | 8/2003 | Ghosh et al. | 510/392 |
| 6,815,193 B2 * | 11/2004 | Poulose et al. | 435/220 |
| 6,831,053 B1 * | 12/2004 | Ghosh et al. | 510/392 |
| 6,838,425 B2 * | 1/2005 | Ghosh et al. | 510/392 |
| 6,927,055 B2 * | 8/2005 | Poulose et al. | 435/219 |

* cited by examiner

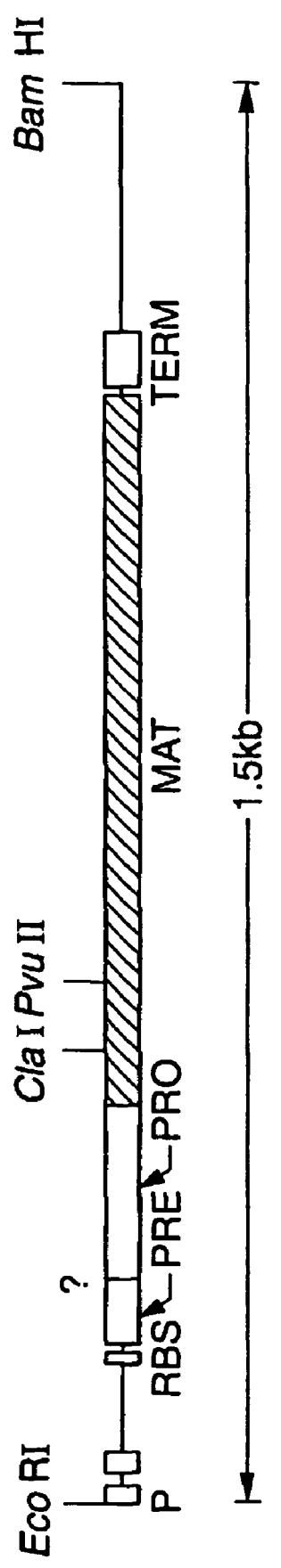
FIG._1A

```
                                                              -107
                                            RBS                Met
GGTCTACTAAAATATTATTCCATACTATACAATTAATACACAGAATAATCTGTCTATTGGTTATTCTGCAAATGAAAAAAGGAGGATAAAGA GTG

-100                      -90                        -80
Arg Gly Lys Lys Val Trp Ile Ser Leu Leu Phe Ala Leu Ile Phe Thr Met Ala Phe Gly Ser Thr Ser
AGA GGC AAA AAA GTA TGG ATC AGT TTG CTG TTT GCT TTA ATC TTT ACG ATG GCG TTC GGC AGC ACA TCC
                                    PRE

-70                       -60
Ser Ala Gln Ala Ala Gly Lys Lys Asp Lys Lys Val Ile Tyr Val Gly Phe Lys Gln Thr Met Ser Thr Met
TCT GCC CAG GCG GCA GGG AAA AAG AAA GAT GCG TTA TAT ATT GTC GGG TTT AAA CAG ACA ATG AGC ACG ATG
                                    PRO

-50                                     -40
Ser Ala Ala Lys Lys Lys Lys Asp Val Ile Ser Glu Lys Gly Gly Lys Val Gln Lys Gln Phe Lys Tyr Val
AGC GCC GCT AAG AAG AAA GAT GTC ATT TCT GAA AAA GGG AAA GTG CAA AAG CAA TTC AAA TAT GTA

-30                                -20                            -10
Ala Ser Ala Thr Leu Asn Ala Tyr Lys Lys Ala Val Ser Val Pro Tyr Gly Val Ser Pro Ala Leu His Ser Gln
GCT TCA GCT ACA TTA AAC GCC TAC AAG AAA GCT GTA TCC GTG CCT TAC GGC GTC AGC CCG GCT CTG CAC TCT CAA

-1 +1                10                              20                         30
His Val Ala His Ala Tyr Ala Gln Ser Gln Ala Leu Glu Gln Ala Tyr Ala Lys Ala Pro Ser His Ser Lys Val
CAC GTA GCA CAT GCG TAC GCG CAG TCC CAG GCG CTG GAA CAG GCT TAC GCT AAA GCC CCT TCT CAT TCT AAG GTA
                  MAT

40
Gly Tyr Thr Gly Ser Asn Val Lys Val Ala Val Val Asp Ser Gly Ile Asp Ser Ser His Pro Asp Leu Lys Val
GGC TAC ACT GGA TCA AAT GTT AAA GTA GCG GTT GTT GAC AGC GGT ATC GAC TCT TCT CAT CCT GAT TTA AAG GTA
```

*FIG._1B - 1*

| 549 | Ala GCA | Gly GGC | Gly GGA | Ala GCC | Ser AGC | Met ATG | Val GTT | Pro CCT | Ser TCT | Glu GAA | Thr ACA | Phe TTC | Gln CAA | Asp GAC | Asn AAC | Ser TCT | His CAC | Gly GGA | Thr ACT | His CAC | Val GTT | Ala GCC |
|---|---|---|---|---|---|---|---|---|---|---|---|---|---|---|---|---|---|---|---|---|---|---|

Position markers: 50, 60 (Asp), 80 (Pro Asn), 90

| 624 | Gly GGC | Thr ACA | Val GTT | Ala GCG | Ala GCT | Asp GAC | Ala GCT | Leu CTT | Gly GGT | Val GTA | Pro CCT | Ser AGC | Asn AAC | Gly GGT | Val GTT | Ala GCG | Pro CCA | Ser AGC | Ser TCA | Ala GCA | Leu CTT | Tyr TAC | Ala GCT | Val GTA | Lys AAA |

Position markers: 70, 100 (Asp Ala), 110

| 699 | Val GTT | Leu CTC | Gly GGT | Asp GAC | Ala GCT | Asn AAC | Met ATG | Ser AGC | Leu CTC | Gly GGC | Gln CAA | Tyr TAC | Ser AGC | Trp TGG | Ile ATC | Gly GGA | Ile ATT | Asn AAC | Ala GCA | Ala GCT | Ile ATC | Ala GCG | Ala GCA | Asn AAC | Met ATG |

Position markers: 120, 130, 140

| 774 | Asp GAC | Val GTT | Ile ATT | Asn AAC | Met ATG | Ser AGC | Leu CTC | Gly GGC | Gly GGA | Pro CCT | Ser TCT | Gly GGT | Ala GCT | Ala GCA | Val GTT | Thr ACA | Asp GAT | Lys AAA | Ala GCC | Val GTT | Ala GCA |

Position markers: 150, 160

| 849 | Ser TCC | Gly GGC | Val GTC | Val GTA | Val GTT | Ala GCG | Ala GCA | Ala GCA | Val GCA | Val GTA | Gly GCA | Ala GCG | Val GTT | Ser TCA | Ser AGC | Ser TCA | Thr ACA | Val GTG | Gly GGC | Tyr TAC | Pro CCT | Gly GGT |

Position markers: 170, 180, 190

| 924 | Lys AAA | Tyr TAC | Pro CCT | Ser TCT | Val GTC | Met ATT | Ala GCA | Val GCG | Gly GGC | Ala GCA | Val GTA | Ser TCT | Ile ATC | Gln CAA | Ser AGC | Thr ACG | Leu CTT | Pro CCT | Gly GGA | Asn AAC | Lys AAA | Tyr TAC | Ser AGC | Phe TTC | Lys AAA | Tyr TAC | Ser AGC | Val GTA | Gly GCG | Ala GCG | Tyr TAC |

Position markers: 200, 210

| 999 | Glu GAG | Leu CTT | Asp GAT | Val GTC | Met ATG | Ala GCA | Pro CCT | Gly GGC | Val GTA | Ser TCT | Ile ATC | Gln CAA | Ser AGC | Thr ACG | Leu CTT | Pro CCT | Gly GGA | Asn AAC | Lys AAA | Tyr TAC | Gly GGG | Ala GCG | Tyr TAC | Pro CCT | Gly GGT |

Position markers: 220, 230, 240

| 1074 | Thr ACG | Ser TCA | Met ATG | Ala GCA | Gly GGA | Ala GCG | Ala GCT | Ala GCT | Leu GCT | Ile TTG | Leu CTT | Ser TCT | Lys AAG | His CAC | Pro CCG | Tyr TAC | Thr ACA | Asn AAC | Trp TGG | Asn AAC | Thr ACT |

*FIG._1B-2*

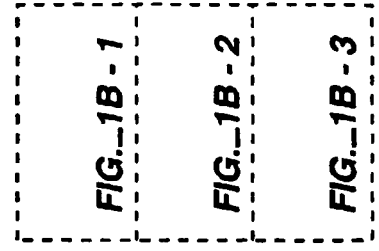
FIG._1B

Conserved Residues in Subtilisins from
*Bacillus Amyloliquefaciens*

COMPARISION OF SUBTILISIN SEQUENCES FROM:
B.amyloliquefaciens
B.subtilis
B.licheniformis
B.lentus

```
        170        180        190
161 SSS..TVGGYPGKYPSVIAVGAVDSSNQRASFSSVGPELDVMA
    S.TSTVGGYPAKYPSTHIAVGAVNSNQRASFSSAGSELDVMA
    STNTIGSYPAKYDSVIAVGAVDSNNRASFSSVGAELEVMA
    S....HSYPARYANAMAVGATDQNNRASFSQYGAGLDIVA 210        220        230
201 PGVSIQSTLPGNKYGAYNGTSMASPHVAGAAALILSKHPN
    PGVSIQSTLPGGTYGAYNGTSMATPHVAGAAALILSKHPT
    PGAGVYSTYPTNTYATLNGTSMATPHVAGAAALIHSKHPN
    PGVNVQSTYPGSTYASLNGTSMATPHVAGAAALVKQKNPS 250        260        270
241 WTNTQVRSSLENTTKLGDSFYYGKLINVQAAAQ
    WTNAQVRDRLSSTATYLGNSFYYGKLINVQAAAQ
    LSASQVRNRLSSTATYLGSSFYYGKLINVEAAAQ
    WSNVQIRNHLKNTATSLGSTNLYGSGLVNAEAATR
```

FIG._3B

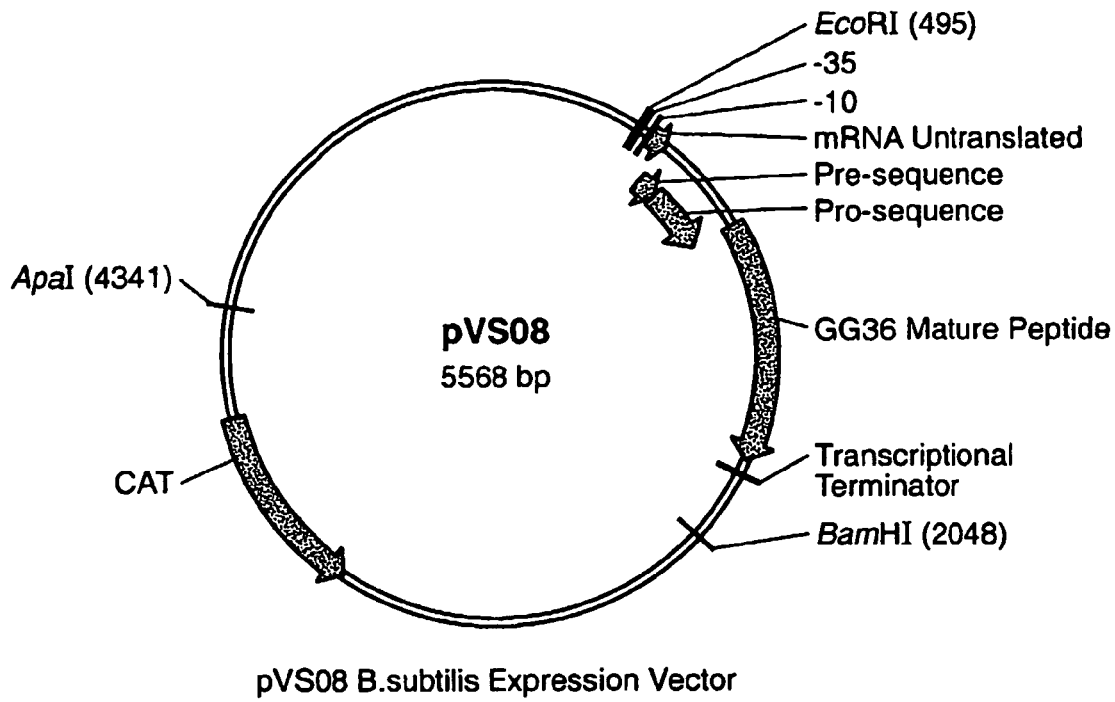
pVS08 B.subtilis Expression Vector
FIG._4
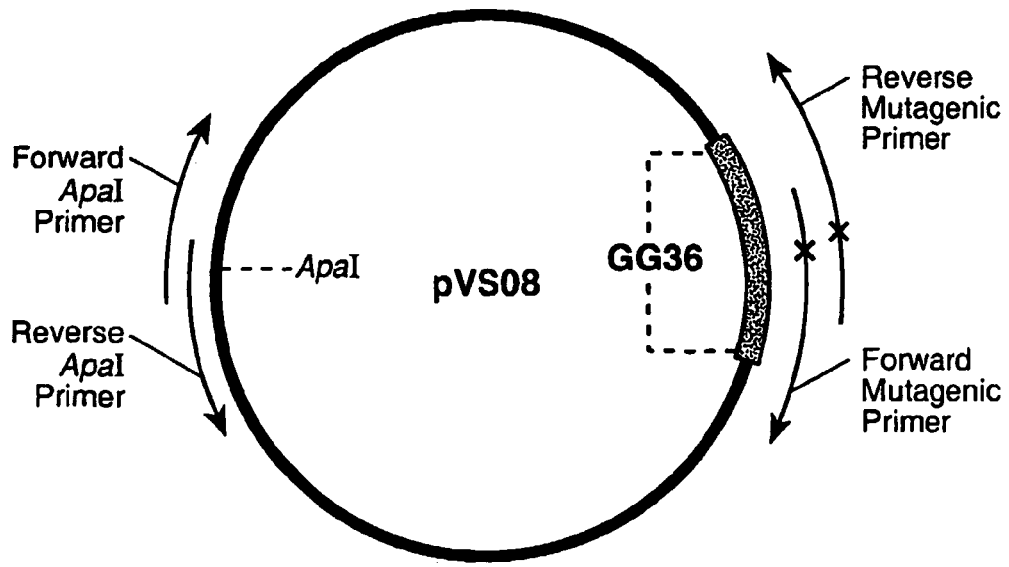
FIG._5

US 7,306,937 B2

MULTIPLY-SUBSTITUTED PROTEASE VARIANTS

BACKGROUND OF THE INVENTION

Serine proteases are a subgroup of carbonyl hydrolases. They comprise a diverse class of enzymes having a wide range of specificities and biological functions. Stroud, R. *Sci. Amer.*, 131:74-88. Despite their functional diversity, the catalytic machinery of serine proteases has been approached by at least two genetically distinct families of enzymes: 1) the subtilisins and 2) the mammalian chymotrypsin-related and homologous bacterial serine proteases (e.g., trypsin and S. gresius trypsin). These two families of serine proteases show remarkably similar mechanisms of catalysis. Kraut, J. (1977), *Annu. Rev. Biochem.*, 46:331-358. Furthermore, although the primary structure is unrelated, the tertiary structure of these two enzyme families bring together a conserved catalytic triad of amino acids consisting of serine, histidine and aspartate.

Subtilisins are serine proteases (approx. MW 27,500) which are secreted in large amounts from a wide variety of *Bacillus* species and other microorganisms. The protein sequence of subtilisin has been determined from at least nine different species of *Bacillus*. Markland, F. S., et al. (1983), *Hoppe-Seyler's Z. Physiol. Chem.*, 364:1537-1540. The three-dimensional crystallographic structure of subtilisins from *Bacillus amyloliquefaciens, Bacillus* licheniforimis and several natural variants of *B. lentus* have been reported. These studies indicate that although subtilisin is genetically unrelated to the mammalian serine proteases, it has a similar active site structure. The x-ray crystal structures of subtilisin containing covalently bound peptide inhibitors (Robertus, J. D., et al. (1972), *Biochemistry*, 11:2439-2449) or product complexes (Robertus, J. D., et al. (1976), *J. Biol. Chem.*, 251:1097-1103) have also provided information regarding the active site and putative substrate binding cleft of subtilisin. In addition, a large number of kinetic and chemical modification studies have been reported for subtilisin; Svendsen, B. (1976), *Carlsberg Res. Commun.*, 41:237-291; Markland, F. S. Id.) as well as at least one report wherein the side chain of methionine at residue 222 of subtilisin was converted by hydrogen peroxide to methionine-sulfoxide (Stauffer, D. C., et al. (1965), *J. Biol. Chem.*, 244:5333-5338) and extensive site-specific mutagenesis has been carried out (Wells and Estell (1988) *TIBS* 13:291-297)

SUMMARY OF THE INVENTION

One aspect of the invention, the charge distribution of a molecule is altered to affect its orientation and interaction with phases, surfaces, other molecules and fields.

An enzyme variant of a precursor or parent enzyme is contemplated herein, the variant comprising one or more modifications at a charged amino acid residue position, the variant being characterized by having the same net electrostatic charge and/or the same isoelectric point as the precursor enzyme.

In another aspect of the present invention, a protease variant of a precursor protease is contemplated herein, the variant comprising one or more modifications at a charged amino acid residue position, the variant being characterized by having the same net electrostatic charge or Isoelectric point as the precursor protease. The charged amino acids can be aspartic acid, glutamic acid, histidine, lysine, tyrosine and arginine. The residue positions can be those equivalent to positions 5, 7, 23, 26, 28-31, 34, 47, 63, 65, 66, 69, 70, 73, 82-85, 88, 90, 92, 93, 105, 113, 125, 138, 139, 148-151, 176, 178, 179, 193, 196, 200, 201, 202, 207, 219, 220, 223, 229, 233, 250, 266, 267 and 273 of *Bacillus amyloliquefaciens* subtilisin (SEQ ID NO:3) are identified herein. The residue positions can also be those equivalent to positions 27, 39, 41, 45, 67, 94, 136, 170, 181, 247, 251 and/or 271 of *Bacillus amyloliquefaciens* subtiuisin (SEQ ID NO:3). It is a further aspect to provide DNA sequences encoding such protease variants, as well as expression vectors containing such variant DNA sequences.

A protease variant of a precursor protease, said variant comprising one or more modifications at a charged amino acid residue position, said variant being characterized by having the same net electrostatic charge as said precursor protease. The protease variant of claim 1, wherein said charged amino acid is selected from the group consisting of aspartic acid, glutamic acid, lysine and arginine. The protease variant comprises an amino acid sequence having a substitution at one or more residue positions equivalent to residue positions selected from the group consisting of 27, 45, 170, 181, 251 and 271 of *Bacillus amyloliquefaciens* subtilisin as set forth In (SEQ ID NO:3). The protease variant comprising a substitution at one or more positions corresponding to 27, 45, 170, 181, 251 and 271 is a substitution selected from K27T, R45N, R170S, D181N, K251G and E271T.

The protease variant may further comprise an additional substitution at one or more positions corresponding to 1, 14, 49, 61, 87, 100, 102, 118, 128, 204 and 258 of *Bacillus amyloliquefaciens* subtilisin as set forth in (SEQ ID NO:3). Variants can be selected from the combinations of R45N-G118E-E271R, R45N-P14R, R45N-N204R, D181N-G118D, R45N-G258R, R170S-A1R, R170S-G61R, R170S-N204R, K251G-S87K, R170S-S21R, E271T-G100E, E271T-G102E, E271T-S128E, K27T-G100E, R170S-G100R, E271T-S49E and E271T-S128E.

Still further, another aspect of the invention is to provide host cells transformed with such vectors.

There is further provided a cleaning composition comprising a protease variant of the present invention.

BRIEF DESCRIPTION OF THE DRAWINGS

FIGS. 1A-C depict the DNA (SEQ ID NO:1) and amino acid sequences (SEQ ID NO:2) for *Bacillus amyloliquefaciens* subtilisin and a partial restriction map of this gene.

FIG. 2 depicts the conserved amino acid residues among subtilisins from *Bacillus amyloliquefaciens* (BPN)' and *Bacillus lentus* (wild-type).

FIGS. 3A and 3B depict the amino acid sequence of four subtilisins. The top line represents the amino acid sequence of subtilisin from *Bacillus amyloliquefaciens* subtilisin (also sometimes referred to as subtilisin BPN') (SEQ ID NO:3). The second line depicts the amino acid sequence of subtilisin from *Bacillus subtilis* (SEQ ID NO:4). The third line depicts the amino acid sequence of subtilisin from *B. licheniformis* (SEQ ID NO:5). The fourth line depicts the amino acid sequence of subtilisin from *Bacillus lentus* (also referred to as subtilisin 309 in PCT WO89/06276) (SEQ ID NO:6). The symbol * denotes the absence of specific amino acid residues as compared to subtilisin BPN'.

FIG. 4 depicts the pVS08 *B. subtilis* expression vector.

FIG. 5 depicts the orientation of the forward ApaI primer, the reverse ApaI primer, the reverse mutagenic primer, and the forward mutagenic primer.

DETAILED DESCRIPTION OF THE INVENTION

Proteases are carbonyl hydrolases which generally act to cleave peptide bonds of proteins or peptides. As used herein, "protease" means a naturally-occurring protease or a recombinant protease. Naturally-occurring proteases include α-aminoacylpeptide hydrolase, peptidylamino acid hydrolase, acylamino hydrolase, serine carboxypeptidase, metallocarboxypeptidase, thiol proteinase, carboxyl-proteinase and metalloproteinase. Serine, metallo, thiol and acid proteases are included, as well as endo and exo-proteases.

The present invention includes protease enzymes which are non-naturally occurring carbonyl hydrolase variants (protease variants) having a different proteolytic activity, stability, substrate specificity, pH profile and/or performance characteristic as compared to the precursor carbonyl hydrolase from which the amino acid sequence of the variant is derived. Specifically, such protease variants have an amino acid sequence not found in nature, which is derived by substitution of a plurality of amino acid residues of a precursor protease with different amino acids. The precursor protease may be a naturally-occurring protease or a recombinant protease.

The protease variants useful herein encompass the substitution of any of the nineteen naturally occurring L-amino acids at the designated amino acid residue positions. Such substitutions can be made in any precursor subtilisin (procaryotic, eucaryotic, mammalian, etc.). Throughout this application reference is made to various amino acids by way of common one- and three-letter codes. Such codes are identified in Dale, M. W. (1989), *Molecular Genetics of Bacteria*, John Wiley & Sons, Ltd., Appendix B.

The protease variants useful herein are preferably derived from a *Bacillus* subtilisin. More preferably, the protease variants are derived from *Bacillus lentus* subtilisin and/or subtilisin 309.

Subtilisins are bacterial or fungal proteases which generally act to cleave peptide bonds of proteins or peptides. As used herein, "subtilisin" means a naturally-occurring subtilisin or a recombinant subtilisin. A series of naturally-occurring subtilisins is known to be produced and often secreted by various microbial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus, is aspartate-histidine-serine. In the chymotrypsin related proteases, the relative order, however, is histidine-aspartate-serine. Thus, subtilisin herein refers to a serine protease having the catalytic triad of subtilisin related proteases. Examples include but are not limited to the subtilisins identified in FIG. 3 herein. Generally and for purposes of the present invention, numbering of the amino acids in proteases corresponds to the numbers assigned to the mature *Bacillus amyloliquefaciens* subtilisin sequence presented in FIG. 1.

"Recombinant subtilisin" or "recombinant protease" refer to a subtilisin or protease in which the DNA sequence encoding the subtilisin or protease is modified to produce a variant (or mutant) DNA sequence which encodes the substitution, deletion or insertion of one or more amino acids in the naturally-occurring amino acid sequence. Suitable methods to produce such modification, and which may be combined with those disclosed herein, include those disclosed in U.S. patent RE 34,606, U.S. Pat. No. 5,204,015 and U.S. Pat. No. 5,185,258, U.S. Pat. No. 5,700,676, U.S. Pat. No. 5,801,038, and U.S. Pat. No. 5,763,257.

"Non-human subtilisins" and the DNA encoding them may be obtained from many procaryotic and eucaryotic organisms. Suitable examples of procaryotic organisms include gram negative organisms such as *E. coli* or *Pseudomonas* and gram positive bacteria such as *Micrococcus* or *Bacillus*. Examples of eucaryotic organisms from which subtilisin and their genes may be obtained include yeast such as *Saccharomyces cerevisiae*, fungi such as *Aspergillus* sp.

An "enzyme variant" has an amino acid sequence which is derived from the amino acid sequence of a "precursor enzyme". The precursor enzymes proteases include naturally-occurring enzymes and recombinant enzymes. Enzymes contemplated by the inventors include, but are not limited to oxidoreductases, transferases, hydrolases, lyases, isomerases, and ligases. Specific exemplary enzymes contemplated by the inventors include, but are not limited to amylases, laccases, proteases, dehydrogenases, and permeases. The amino acid sequence of the enzyme variant is "derived" from the precursor enzyme amino acid sequence by the substitution, deletion or insertion of one or more amino acids of the precursor amino acid sequence. Such modification is of the "precursor enzyme DNA sequence" which encodes the amino acid sequence of the precursor enzyme rather than manipulation of the precursor enzyme per se. Suitable methods for such manipulation of the precursor DNA sequence include methods disclosed herein, as well as methods known to those skilled in the art. It is contemplated that any reference or discussion regarding proteases may be applicable to other enzymes, e.g., those identified in part above.

A "protease variant" has an amino acid sequence which is derived from the amino acid sequence of a "precursor protease". The precursor proteases include naturally-occurring proteases and recombinant proteases. The amino acid sequence of the protease variant is "derived" from the precursor protease amino acid sequence by the substitution, deletion or insertion of one or more amino acids of the precursor amino acid sequence. Such modification is of the "precursor DNA sequence" which encodes the amino acid sequence of the precursor protease rather than manipulation of the precursor protease enzyme per se. Suitable methods for such manipulation of the precursor DNA sequence include methods disclosed herein, as well as methods known to those skilled in the art (see, for example, EP 0 328299, WO89/06279 and the US patents and applications already referenced herein).

"Charged amino acid" is defined as an amino acid that is potentially ionizable, changes charge and provides an electrostatic charge at a specified pH or pH range. These amino acids include, for example, acidic amino acids, basic amino acids and some polar amino acids. Acidic amino acids are those that are negatively charged at pH 6.0, for example aspartic acid (Asp or D) and/or glutamic acid (Glu or E). Basic amino acids are those that are positively charged at pH 6.0, for example lysine (Lys or K), arginine (Arg or R), and/or Histidine (His or H).

"Uncharged amino acid" is defined as an amino acid that is not potentially ionizable. These amino acids include, but are not limited to uncharged nonpolar amino acids and/or uncharged polar amino acids. Uncharged nonpolar amino acids include, but are not limited to alanine (Ala or A), valine (Val or V), leucine (Leu or L), isoleucine (Ile or I), proline (Pro or P), phenylalanine (Phe or F), tryptophan (Trp or W), and/or methionine (Met or M). Uncharged polar amino acids include, but are not limited to glycine (Gly or G), serine (Ser or S), threonine (Thr or T), cysteine (Cys or C), tyrosine (Tyr or Y), asparagine (Asn or N) and/or glutamine (Gln or Q).

"Net electrostatic charge" is defined as the sum of the electrostatic charges of the variant or precursor enzyme or protease at a given pH or pH range. An exemplary pH is pH 6.0.

"Isoelectric Point" ($pI_o$) is defined as the pH value where the protein or protein complex, e.g., the protease or protease complex (with optionally attached metal or other ions) is neutral, i.e. the sum of electrostatic charges (net electrostatic charge=NEC) on the complex is equal to zero. In this sum consideration of the positive or negative nature of the individual electrostatic charges must be taken into account.

The same isoelectric point ($pI_o$) is defined as the $pI_o$ being within a defined range of pH units. For example, a defined range of pH units could be no greater than 1 pH unit, between 0.25 and 0.75, for example 0.5 pH units, preferably within 0.01 and 0.5 pH units, for example 0.1 pH units, and more preferably within 0.001 and 0.05 pH units, for example 0.01 pH units of the $pI_o$ to which the other $pI_o$ is being compared. The same isoelectric point can be determined at a given pH or at a defined pH range.

"Identical electrostatic charge" is defined as maintaining "Z" or the same number of specific charged residues in the protease variant as there are in the precursor protease. While the number of the charged residues may be the same, the specific amino acid residues may be substituted into other positions about the exterior of the protease variant so long as the net electrostatic charge is the same as that of the precursor protease at a given pH.

The "same net electrostatic charge" is defined as maintaining Z, or the sum of the electrostatic charges of the protease precursor within a defined range of the sum of electrostatic charges of the protease variant. Maintaining the same sum of electrostatic charge means keeping the net electrostatic charge within a defined range of charge units over a defined range of pH. A protease variant having the same net electrostatic charge as the protease precursor would have a net electrostatic charge within a defined number of charge units of the precursor protease. For example, the protease variant having the same net electrostatic charge can be no greater than 1 pH unit, within 0.25 to 0.75 charge units, e.g., 0.5 units, of the precursor protease net electrostatic charge. Still more preferably the protease variant having the same net electrostatic charge can be within 0.05 to 0.25 units, e.g., 0.1 units of the precursor protease net electrostatic charge. Still more preferably the protease variant having the same net electrostatic charge can be within 0.001 to 0.05 units, e.g., 0.01 units of the precursor protease net electrostatic charge. Charge units can be defined as the number of protons donated (acid) or accepted (basic). The electrostatic charge of an individual amino acid can be generally ascertained by determining the number of protons accepted or donated at a given pH, for example 6.0 or 7.0. Z values can also be determined by the equations described later in this application.

"Total charge content" of the variant or precursor protease is defined as the total number of electrostatic charges of the respective protease. A protease variant with the same net electrostatic charge may have a different total charge content as the precursor protease.

As recognized by those of skill in the art, the isoelectric point can be conveniently calculated by using equilibrium considerations using pK values for the various charged residues in the enzyme in question and then finding by iteration the pH value where the NEC of the enzyme molecule is equal to zero as described in EP 0945 502 and the examples therein, which is expressly incorporated by reference herein.

One problem with this calculation is that the pK values for the charged residues are dependent on their environment and consequently subject to variation. However, very good results are obtainable by allocating specific approximate pK values to the charged residues independently of the actual value. It is also possible to perform more sophisticated calculations, partly taking the environment into consideration.

The $pI_o$ may also be determined experimentally by isoelectric focusing or by titrating a solution containing the enzyme. In addition, the various pK values for is the charged residues may be determined experimentally by titration.

In a further aspect of the invention, the above observations about the $pI_o$ are further utilized in a method for determining or selecting the position(s) and the amino acid(s) to be deleted, substituted or inserted for the amino acid(s) in the precursor protease, so that the net electrostatic charge or isoelectric point of the variant protease is the same as the NEC or the $pI_o$ of the precursor protease calculated at the same pH value or a defined pH range.

Another way of expressing this principle covered by the invention is that the position(s) and the amino acid(s) to be deleted, substituted or inserted for the amino acid(s) in said precursor protease or enzyme is selected in a way whereby the total number of charges or total charge content (=TCC) and/or the NEC in a resulting variant protease or enzyme is kept constant to provide for a variant protease or enzyme having an isoelectric point kept the same at a defined pH or pH range for optimum wash performance of the protease or enzyme, which pH optimum should be as close as possible to the pH of the wash liquor, wherein said mutant protease is intended for use.

As indicated above, the $pI_o$ of a macromolecule such as an enzyme is calculated as the pH where the NEC of the molecule is zero. The procedure is exemplified in the examples described in EP 0 945 502, but the principles are described in more detail here.

pK values are assigned to each potentially charged amino acid residue. Then the ratio of the occurrence of an amino acid residue at a given pH in charged or uncharged form (charged/uncharged, C/U(i)) is calculated for both negative and positive charges by using formulas Ia and Ib:

$$C/U(i)=10^{(pH-pKi)} \text{(negative charge)} \quad \text{(Ia)}$$

$$C/U(i)=10^{(pKi-pH)} \text{(positive charge)} \quad \text{(Ib)}.$$

According to the above formulas, if pH equals $pK_i$, C/U(i) is equal to 1.

The relative charge, $Q_r(i)$, or charge contribution allocated to each charged residue is then calculated by using formulas IIa and IIb:

$$Q_r(i)=C/U(i)/(1+C/U(i)) \text{(negative charge)} \quad \text{(IIa)}$$

$$Q_r(i)=-C/U(i)/(1+C/U(i)) \text{(positive charge) (IIb)}.$$

The pH value where the sum of all the charge contributions from the charged residues is equal to zero is can be found by iteration or through interpolation in a sufficiently dense pH-charge sum table.

Those skilled in the art will recognize that another method of determining the net electrostatic charge Z as, if the group (such as the R or amino group) has a cationic acid form, α represents the fractional positive charge:

$$Z = +\alpha = \frac{+1}{1 + 10^{(pH-pKa)}}$$

On the other hand, for groups such as the carboxyl, with a neutral acid form and an anionic conjugate base, α represents the fraction uncharged. The fractional charge is then:

$$Z = -(1-\alpha) = \alpha - 1 = \frac{-1}{1 + 10^{(pKa-pH)}}$$

It has been noted that various bulk protease or enzyme properties are dependent upon the NEC and/or isoelectric point of the protease or enzyme molecule. For example, the protease or enzyme solubility, stability, phase distribution in multiple phase media and/or surface charge are properties that are affected by an alteration of the molecule's NEC and/or isoelectric point. Surprisingly, improved protease characteristics can be effected while maintaining the same isoelectric point or same net electrostatic charge. While not desiring to be bound by a particular theory, it is believed by the inventors that there are situations where it is desirous to maintain the bulk properties of the protein, enzyme, or protease in question while modifying the kinetics of the interaction of the molecule, e.g. the distribution of charges or orientation of the molecule relative a substrate, surface or media.

In one aspect of the invention, the protease variant and the precursor protease have an identical net electrostatic charge or identical isoelectric point. The same net electrostatic charge can be maintained by having the identical electrostatic charge or compensating for the charge change resulting from the additionally modified positions by additional modifications to the amino acid sequence of the precursor protease. These additional modifications include, but are not limited to substituting or inserting a residue that has an opposite charge to that additional residue (adding an additional acidic residue to compensate for an additional basic residue). Thus it is contemplated that the number of charged residues in the protease variant may be different from that of the protease precursor, for example, when the number of charged residues is greater than in the protease precursor. To compensate for the additional charged residue, a correspondingly oppositely charged amino acid substitution can be made to maintain the same net electrostatic charge. Additionally, the number of charged residues in the protease or enzyme variant may be less than the number of charged residues in the protease or enzyme precursor if a correspondingly oppositely charged amino acid deletion or substitution of another uncharged residue when a charged residue is deleted or substituted with an uncharged residue.

In one aspect of the present invention, is when the NEC or pI$_o$ is identical, for example when the total charge content of the protease variant and the precursor protease are the same; or when the same number of charged residues in the precursor protease is maintained. When the charged amino acid is repositioned to maintain the identical NEC or pIo, at least one of these charged amino acids is substituted into a different residue position from that of the precursor protease.

If there are a specified number of a specific charged amino acid in the protease precursor, "X" lysines in *Bacillus lentus* (GG36), then the variant protease will retain the same number of lysine residues, i.e., "X", but at different positions relative to the precursor protease. Thus, for example, K27 can be substituted with a different residue and the corresponding K substituted at another position, preferably a surface position. In one embodiment, a charged residue, e.g., glutamic acid, aspartic acid, lysine or arginine can be substituted into a different position. To maintain the identical electrostatic charge, the specific precursor residue which is replaced by the charged residue, e.g., K residue from position 27, can be substituted in at position 27. For example an R45N-N204R has identical residue positions replaced to maintain identical electrostatic charge. In addition, if the specific precursor residue which is replaced by the charged residue is an uncharged residue, other uncharged residues can be substituted into a position originally having a charged residue. For example an R170S-A1R combination replaces an alanine with an arginine while replacing an arginine with a serine. Of course, if multiple modifications are made, any replaced residue can be substituted into any of the other residues being modified so long as the same number of each respective amino acid is maintained. The electrostatic charge can be determined at any predetermined pH, so long as the determination is made at the same pH for the protease variant and the precursor protease.

In another aspect of the invention, the same net electrostatic charge of the molecule is maintained by compensating for the change in net electrostatic charge resulting from the modification to the precursor protease. For example, one way to achieve such alteration is to insert or substitute in an additional oppositely charged amino acid residue or delete a similarly charged but different amino acid residue. If, for example, there are more acidic amino acids present in the protease variant than in the precursor protease, the variant will include additional basic amino acids. If, for example, there are more of a specific acidic amino acid, for example, glutamic acid, present in the protease variant than in the precursor protease, to compensate for such modifications, a corresponding number of aspartic acid residues could be deleted or substituted with a non-charged amino acid. For example, if there is a specified number of a charged amino acids in the precursor protease, the inventors contemplate increasing or decreasing the number of that amino acid in the variant protease with a corresponding increase or decrease in the amino acids that compensate for the change in the number of charged amino acids. Thus, as described above, additional positively charged residues could be compensated by the addition of a corresponding number of negatively charged amino acids or substitution of a corresponding number of other positively charged amino acids with a non-charged residue or combinations thereof. A lesser number of positively charged residues could be compensated by the deletion of a corresponding number of negatively charged amino acids, substitution of a corresponding number of non-charged residues for a corresponding number of negatively charged amino acids or combinations thereof.

In one embodiment, the same charged amino acid residue that is replaced by an uncharged residue at a first amino acid position is substituted into a second amino acid position where the same uncharged amino acid replacing the charged residue is present. An uncharged residue can be substituted at the original position of the charged amino acid, while the substituted charged amino acid can replace the position of the uncharged amino acid. For example, R45N-N204R reflects the substitution of an uncharged amino acid, asparagine for a charged amino acid, arginine. The same uncharged amino acid substituted for the charged amino acid need not be present at the position where the charged amino acid is reinserted. For example, an uncharged amino acid selected from the group of alanine (Ala or A), glycine (Gly or G), asparagines (Asn or N), proline (Pro or P), serine (Ser or S) and/or threonine (Thr or T) can be substituted into the charged amino acid position while the charged amino acid residue is substituted into an amino acid position originally occupied by another in the above group. For example, in the variant E271T-G100E, the glutamic acid amino acid at position 271 is substituted with a threonine amino acid, while a glycine residue at position 100 is replaced with a glutamic acid amino acid. Like wise, the identical charged amino acid need not be substituted into the originally uncharged position, e.g., K27T-G100E. The charged amino acids aspartic acid (D), glutamic acid (E), lysine (K), and arginine (R) are useful in this regard.

In still another aspect of the invention the protease variant NEC varies less than a range of 0.5 charge units (Z) from that of the precursor protease NEC over the range of pH's from 0-14.

In still another aspect of the invention, the protease variant NEC varies less than a range of 1 charge unit from that of the precursor protease NEC over a defined pH range. That defined pH range could be, for example within 2 pH units of the that recognized in the art as the optimum or desired pH for the desired protease or enzyme environment or within a range of 4 pH units.

In another aspect of the invention, it has been determined that the modification of the charged residues found in the precursor protease while maintaining the same or identical net electrostatic charge can result in a protease variant displaying increased beneficial wash characteristics.

In still another aspect of the invention, it has been determined that the modification of the charged residues found in the precursor protease while maintaining the same or identical net electrostatic charge at a defined pH, over a defined pH range, e.g. over a range of 4 pH units, or over the range of pH from 0.001 to 14 can result in a protease variant displaying increased beneficial wash characteristics.

Exemplary charged amino acid residues contemplated for modification by the inventors include, for example, basic amino acids such as lysine, arginine and/or histidine; acidic amino acids, for example aspartic acid and/or glutamic acid; and/or otherwise polar R groups, for example tyrosine. A-2

In another aspect, the variant proteases of the present invention have, relative to said precursor protease, the same number of positively-charged amino acid residue(s), both the identical amino acids as in the precursor protease and different amino acids having the same charge, and the same number of negatively-charged amino acid residue(s) as in the precursor protease; or either more or fewer positively-charged amino acid residue(s) and a corresponding more or fewer negatively-charged amino acid residue(s), such that the net electrostatic charge and/or the isoelectric point of the protease variant is the same as the precursor protease, while having modifications among the equivalent amino acid residues at any one or more of positions: 5, 7, 22, 23, 24, 26, 28-31, 34, 45, 47, 63, 65, 66, 69, 70, 73, 82-85, 88, 90, 92, 93, 97, 102, 105, 113, 125, 127, 138, 139, 148-151, 169, 170, 176, 178, 179, 193, 196, 200, 201, 202, 207, 219, 220, 223, 229, 233, 250, 266, 267 and 273 of Bacillus amyloliquefaciens (BPN') (SEQ ID NO:3). In one embodiment, modifications among the equivalent amino acid residues at one or more of positions 27, 45, 136, 170, 181, 247, 251 and/or 271 include the substitution of an uncharged residue for a charged residue position. These residue positions are of interest since these equivalent positions in Bacillus lentus wild type have charged amino acid residues at these positions. For example, the residue positions at 27, 38, 40, 44, 65, 92, 134, 164, 175, 241, 245, and/or 265 of Bacillus lentus subtilisin (SEQ ID NO:6) are equivalent, respectively, to 27, 39, 41, 45, 67, 94, 136, 170, 181, 247, 251 and/or 271 of Bacillus amyloliquefacien (SEQ ID No:2).

In another aspect, the variant proteases of the present invention have, relative to said precursor protease, the same number of positively-charged amino acid residue(s), both the identical amino acids as in the precursor protease and different amino acids having the same charge, and the same number of negatively-charged amino acid residue(s) as in the precursor protease; or either more or fewer positively-charged amino acid residue(s) and a corresponding more or fewer negatively-charged amino acid residue(s), such that the net electrostatic charge and/or the isoelectric point of the protease variant is the same as the precursor protease, while having modifications among the equivalent amino acid residues at any one or more of positions: 27, 39, 41, 45, 67, 94, 136, 170, 181, 197, 247, 249, 251, and 271 of Bacillus amyloliquefaciens (BPN') (SEQ ID No:3). Specific substitutions contemplated by the inventors include K27A, K27C, K27E, K27Q, K27G, K27H, K27I, K27L, K27M, K27F, K27P, K27S, K27T, K27W, K27Y, H39A, H39R, H39D, $H_{39}N$, $H_{39}C$, H39E, H39Q, H39G, H39H, H39I, H39L, H39K, H39M, $H_{39}F$, H39P, H39T, H39W, H39Y, H39V, D41A, D41R, D41C, D41E, D41Q, D41G, D41H, D41I, D41L, D41K, D41M, D41F, D41P, D41S, D41T, D41W, D41Y, D41V, R45A, R45R, R45D, R45N, R45C, R45E, R45Q, R45G, R45H, R45I, R45L, R45K, R45M, R45F, R45P, R45S, R45T, R45W, R45Y, R45V, H67A, H67R, H67D, $H_{67}N$, $H_{67}C$, H67E, H67Q, H67G, H67H, H67I, H67L, H67K, H67M, $H_{67}F$, H67P, H67S, H67T, H67W, H67Y, H67V, K94A, K94R, K94D, K94N, K94C, K94E, K94Q, K94G, K94H, K94I, K94L, K94K, K94M, K94F, K94P, K94S, K94T, K94W, K94Y, K94V, E136A, E136D, E136N, E136C, E136E, E136G, E136H, E136I, E136L, E136K, E136M, E136F, E136P, E136S, E136T, E136W, E136Y, E136V, R170A, R170R, R170D, R170N, R170C, R170E, R170Q, R170G, R170H, R170I, R170L, R170K, R170M, R170F, R170P, R170S, R170T, R170W, R170Y, R170V, D181A, D181R, D181D, D181N, D181C, D181E, D181O, D181G, D181H, D181I, D181L, D181K, D181M, D181F, D181P, D181S, D181T, D181W, D181Y, D181V, D197A, D197R, D197D, D197N, D197C, D197E, D197Q, D197G, D197H, D197I, D197L, D197K, D197M, D197F, D197P, D197S, D197T, D197W, D197Y, D197V, R247A, R247R, R247D, R247N, R247C, R247E, R247Q, R247G, R247H, R247I, R247L, R247K, R247M, R247F, R247P, R247S, R247T, R247W, R247Y, R247V, H249A, H249R, H249D, H249N, H249C, H249E, H249Q, H249G, H249H, H249I, H249K, H249M, H249F, H249P, H249S, H249T, H249W, H249V, K251A, K251D, K251C, K251Q, K251G, K251H, K251I, K251L, K251K, K251M, K251F, K251P, K251S, K251T, K251W, K251Y, K251V, E271A, E271R, E271 D, E271N, E271 C, E271 E, E271H, E271I, E271 L, E271 K, E271M, E271F, E271P, E271S, E271T, E271W, E271Y, and/or E271V of Bacillus amyloliquefaciens (SEQ ID No:3). It was noted that an increase in the number of positive charged residues by substitution thereof may result in an increase in the efficacy of that particular variant in a particular wash environment, while a corresponding opposite charge change could result in increased efficacy in a different wash environment. For example, it is anticipated that negative charge mutations provide beneficial characteristics in low ionic strength wash environments and that positive charge mutations provide beneficial characteristics in high ionic strength wash environments. It is anticipated that variants that encompass both a positive increase and a negative increase while maintaining the same net electrostatic charge or isoelectric point will result in a protease molecule that exhibits improved characteristics in both environments as compared to the performance of the precursor protease.

These substitutions are preferably made in *Bacillus lentus* (recombinant or native-type) subtilisin, although the substitutions may be made in any *Bacillus* protease, for example *Bacillus amyloliquefaciens* and/or Subtilisin 309 (SEQ ID No:6).

One aspect of the present invention includes a protease variant further comprising at least one additional replaced amino acid at one or more residue positions equivalent to residue positions or selected from the group consisting of 1, 2-4,6,9-12, 14, 15,17-20, 25, 27, 36-38, 40, 44, 49, 51, 52, 54-61, 68, 71, 75, 76, 87, 89, 91, 97, 100-102, 104, 108, 111, 112, 115, 117, 118,120-123, 128, 129, 131, 133, 134, 136, 137, 140, 143-146, 159, 164, 165, 167, 170, 171, 173, 175, 180, 182-187, 191, 192, 194, 195, 204, 206, 209-212, 216, 218, 222, 224, 226 234-245, 252, 255, 257-263 265, 268, 269, and 274 of *B. amyloliquefaciens* subtilisns (SEQ ID No:3). Specific substitutions contemplated by the inventors include those equivalent to: I122A, Y195E, M222A, M222S, Y167A, R170S, A194P, D36, N76D, H120D, G195E, and K235N of *Bacillus amyloliquefaciens* (SEQ ID No:3) or *Bacillus lentus*, (SEQ ID No:6) which variant is derived from a *Bacillus* subtilisin.

Of particular interest are variants at these positions demonstrating increased wash performance with a charged amino acid substitution. Combination variants including these positions and those originally having a charged amino acid are of interest. Exemplary combinations contemplated by the inventors include K27T-G100E, R45N-A1R, R45N-P14R, R45N-G61R, R45N-S128R, R45N-N$_2$O$_4$R, R45N-S216R, R45N-G258R, R170S-A1R, R170S-P14R, R170S-S49R, R170S-G61R, R170S-G100R, R170S-S128R, R170S-N$_2$O$_4$R, R170S-S216R, R170S-G258R, D181N-G118D, D181N-G258D, K251G-S87K, E271T-S49E, E271T-T66E, E271T-G100E, E271T-G102E, E271T-S128E, R45N-G118E-E271R, S49R-G102E-R170S-E271T, and P14R-R45N-R170S-G258R. Those skilled in the art will recognize the protease variants having these modifications can be made and are described in U.S. Pat. Nos. 5,741,694; 6,190,900; and 6,197,567, expressly incorporated by reference herein. In addition, these modifications can also be made using direct *Bacillus* transformation methods as described in Provisional Application Ser. No. 60/423,087 (filed Nov. 1, 2002; Neelam Amin and Volker Schellenberger). In one embodiment, the modifications were performed using fusion PCR techniques (Teplyakov, AV, et al, *Protein Eng.*, 1992 Jul 5(5):413-20). Provisional Application Ser. No. 60/440,792, filed concurrently this date (Chris Leeflang, et al.)

Still another aspect of the present invention includes a protease variant further comprising at least one additional replaced amino acid at one or more residue positions from the group consisting of 21, 22, 24, 32, 33, 36, 50, 64, 67, 77, 87, 94, 95, 96, 97, 104, 107, 110, 124, 123, 126, 127, 128, 129, 135, 152, 155, 157, 156, 166, 169, 170, 171, 172, 189, 197, 204, 213, 214, 215, 217, 222, or 274 of *Bacillus amyloliquefaciens* (SEQ ID No:3). Specific residues contemplated by the inventors include: K27R, M50F, N76D, S101G, S103A, V104I, V104Y, I122A, N123S, M124L, G159D, Y217L, A232V, Q236H, Q245R, N248D, N252K, T274A, and M222S. Protease variants, recombinant DNA encoding mutants at these positions and/or methods for making these modifications are described in US patent Nos. RE 34,606; 5,972,682; 5,185,258; 5,310,675; 5,316,941; 5,801,038; 5,972,682, 5,955,340 and 5,700,676, expressly incorporated by reference herein.

These amino acid position numbers refer to those assigned to the mature *Bacillus amyloliquefaciens* subtilisin sequence presented in FIG. 1. The invention, however, is not limited to the mutation of this particular subtilisin but extends to precursor proteases containing amino acid residues at positions which are "equivalent" to the particular identified residues in *Bacillus amyloliquefaciens* subtilisin. In a preferred embodiment of the present invention, the precursor protease is *Bacillus lentus* subtilisin (SEQ ID NO. 6) and the substitutions are made at the equivalent amino acid residue positions in *B. lentus* corresponding to those listed above.

A residue (amino acid) position of a precursor protease is equivalent to a residue of *Bacillus amyloliquefaciens* subtilisin if it is either homologous (i.e., corresponding in position in either primary or tertiary structure) or analogous to a specific residue or portion of that residue in *Bacillus amyloliquefaciens* subtilisin (i.e., having the same or similar functional capacity to combine, react, or interact chemically).

In order to establish homology to primary structure, the amino acid sequence of a precursor protease is directly compared to the *Bacillus amyloliquefaciens* subtilisin primary sequence and particularly to a set of residues known to be invariant in subtilisins for which sequence is known. For example, FIG. 2 herein shows the conserved residues as between *B. amyloliquefaciens* subtilisin and *B. lentus* subtilisin. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of *Bacillus amyloliquefaciens* subtilisin are defined. Alignment of conserved residues preferably should conserve 100% of such residues. However, alignment of greater than 98%, greater than 95%, greater than 90%, greater than 85%, greater than 80%, greater than 75%, greater than 50% or at least greater than 45% of conserved residues is also adequate to define equivalent residues. Conservation of the catalytic triad, Asp32/His64/Ser221 should be maintained. Siezen et al. (1991) *Protein Eng.* 4(7):719-737 shows the alignment of a large number of serine proteases. Siezen et al. refer to the grouping as subtilases or subtilisin-like serine proteases.

For example, in FIG. 3, the amino acid sequence of subtilisin from *Bacillus amyloliquefaciens* (SEQ ID No:3), *Bacillus subtilis* (SEQ ID No:4), *Bacillus licheniformis* (carlsbergensis) (SEQ ID No:5) and *Bacillus lentus* (SEQ ID No:6) are aligned to provide the maximum amount of homology between amino acid sequences. A comparison of these sequences shows that there are a number of conserved residues contained in each sequence. These conserved residues (as between BPN' and *B. lentus*) are identified in FIG. 2.

These conserved residues, thus, may be used to define the corresponding equivalent amino acid residues of *Bacillus amyloliquefaciens* subtilisin in other subtilisins such as subtilisin from *Bacillus lentus* (PCT Publication No. WO89/06279 published Jul. 13, 1989), the preferred protease precursor enzyme herein, or the subtilisin referred to as PB92 (EP 0 328 299), which is highly homologous to the preferred *Bacillus lentus* subtilisin. The amino acid sequences of certain of these subtilisins are aligned in FIGS. 3A and 3B with the sequence of *Bacillus amyloliquefaciens* subtilisin to produce the maximum homology of conserved residues. As can be seen, there are a number of deletions in the sequence of *Bacillus lentus* as compared to *Bacillus amyloliquefaciens* subtilisin. Thus, for example, the equivalent amino acid for Val165 in *Bacillus amyloliquefaciens* subtilisin in the other subtilisins is isoleucine for *B. lentus* and *B. licheniformis*.

"Equivalent residues" may also be defined by determining homology at the level of tertiary structure for a precursor protease whose tertiary structure has been determined by x-ray crystallography. Equivalent residues are defined as those for which the atomic coordinates of two or more of the main chain atoms of a particular amino acid residue of the precursor protease and *Bacillus amyloliquefaciens* subtilisin (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the protease in question to the *Bacillus amyloliquefaciens* subtilisin. The best model is the crystallographic model giving the lowest R factor for experimental diffraction data at the highest resolution available.

$$R \text{ factor} = \frac{\Sigma_h |Fo(h)| - |Fc(h)|}{\Sigma_h |Fo(h)|}$$

Equivalent residues which are functionally similar to a specific residue of *Bacillus amyloliquefaciens* subtilisin are defined as those amino acids of the precursor protease which may adopt a conformation such that they either alter, modify or contribute to protein structure, substrate binding or catalysis in a manner defined and attributed to a specific residue of the *Bacillus amyloliquefaciens* subtilisin. Further, they are those residues of the precursor protease (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *Bacillus amyloliquefaciens* subtilisin. The coordinates of the three dimensional structure of *Bacillus amyloliquefaciens* subtilisin are set forth in EPO Publication No. 0 251 446 (equivalent to U.S. Pat. No. 5,182,204, the disclosure of which is incorporated herein by reference) and can be used as outlined above to determine equivalent residues on the level of tertiary structure.

Some of the residues identified for substitution are conserved residues whereas others are not. In the case of residues which are not conserved, the substitution of one or more amino acids is limited to substitutions which produce a variant which has an amino acid sequence that does not correspond to one found in nature. In the case of conserved residues, such substitutions should not result in a naturally-occurring sequence. The protease variants of the present invention include the mature forms of protease variants, as well as the pro- and prepro-forms of such protease variants. The prepro-forms are the preferred construction since this facilitates the expression, secretion and maturation of the protease variants.

"Prosequence" refers to a sequence of amino acids bound to the N-terminal portion of the mature form of a protease which when removed results in the appearance of the "mature" form of the protease. Many proteolytic enzymes are found in nature as translational proenzyme products and, in the absence of post-translational processing, are expressed in this fashion. A preferred prosequence for producing protease variants is the putative prosequence of *Bacillus amyloliquefaciens* subtilisin, although other protease prosequences may be used.

A "signal sequence" or "presequence" refers to any sequence of amino acids bound to the N-terminal portion of a protease or to the N-terminal portion of a proprotease which may participate in the secretion of the mature or pro forms of the protease. This definition of signal sequence is a functional one, meant to include all those amino acid sequences encoded by the N-terminal portion of the protease gene which participate in the effectuation of the secretion of protease under native conditions. The present invention utilizes such sequences to effect the secretion of the protease variants as defined herein. One possible signal sequence comprises the first seven amino acid residues of the signal sequence from *Bacillus subtilis* subtilisin fused to the remainder of the signal sequence of the subtilisin from *Bacillus lentus* (ATCC 21536).

A "prepro" form of a protease variant consists of the mature form of the protease having a prosequence operably linked to the amino terminus of the protease and a "pre" or "signal" sequence operably linked to the amino terminus of the prosequence.

"Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

The "host cells" used in the present invention generally are procaryotic or eucaryotic hosts which preferably have been manipulated by the methods disclosed in U.S. Patent RE 34,606 and/or U.S. Pat. No. 5,441,882 to render them incapable of secreting enzymatically active endoprotease. A host cell useful for expressing protease is the *Bacillus* strain BG2036 which is deficient in enzymatically active neutral protease and alkaline protease (subtilisin). The construction of strain BG2036 is described in detail in U.S. Pat. No. 5,264,366. Other host cells for expressing protease include *Bacillus subtilis* 1168 (also described in U.S. Patent RE 34,606, U.S. Pat. No. 5,441,882 and U.S. Pat. No. 5,264, 366, the disclosure of which are incorporated herein by reference), as well as any suitable *Bacillus* strain such as *B. licheniformis*, *B. lentus*, etc. A particularly useful host cell is the *Bacillus* strain BG2864. The construction of strain BG2864 is described in detail in D. Naki, C. Paech, G. Ganshaw, V. Schellenberger. Appl Microbiol Biotechnol (1998) 49:290-294.

Host cells are transformed or transfected with vectors constructed using recombinant DNA techniques. Such transformed host cells are capable of either replicating vectors encoding the protease variants or expressing the desired protease variant. In the case of vectors which encode the pre- or prepro-form of the protease variant, such variants, when expressed, are typically secreted from the host cell into the host cell medium.

"Operably linked," when describing the relationship between two DNA regions, simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occurring precursor protease may be obtained in accord with the general methods known to those skilled in the art. The methods generally comprise synthesizing labeled probes having putative sequences encoding regions of the protease of interest, preparing genomic libraries from organisms expressing the protease, and screening the libraries for the gene of interest by hybridization to the probes. Positively hybridizing clones are then mapped and sequenced.

The cloned protease is then used to transform a host cell in order to express the protease. The protease gene is then ligated into a high copy number plasmid. This plasmid replicates in hosts in the sense that it contains the well-known elements necessary for plasmid replication: a promoter operably linked to the gene in question (which may be supplied as the gene's own homologous promoter if it is recognized, i.e., transcribed, by the host), a transcription termination and polyadenylation region (necessary for stability of the mRNA transcribed by the host from the protease gene in certain eucaryotic host cells) which is exogenous or is supplied by the endogenous terminator region of the protease gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosomal limitations. However, it is within the scope herein to integrate multiple copies of the protease gene into host genome. This is facilitated by procaryotic and eucaryotic organisms which are particularly susceptible to homologous recombination.

The gene can be a natural *B. lentus* gene. Alternatively, a synthetic gene encoding a naturally-occurring or mutant precursor protease may be produced. In such an approach, the DNA and/or amino acid sequence of the precursor protease is determined. Multiple, overlapping synthetic single-stranded DNA fragments are thereafter synthesized, which upon-hybridization and ligation produce a synthetic DNA encoding the precursor protease. An example of synthetic gene construction is set forth in Example 3 of U.S. Pat. No. 5,204,015, the disclosure of which is incorporated herein by reference.

Once the naturally-occurring or synthetic precursor protease gene has been cloned, a number of modifications are undertaken to enhance the use of the gene beyond synthesis of the naturally-occurring precursor protease. Such modifications include the production of recombinant proteases as disclosed in U.S. Patent RE 34:606; U.S. Pat. Nos. 5,741,694; 6,190,900; 6,197,567; 5,972,682; 5,185,258; 5,700,676 and EPO Publication No. 0 251 446 and the production of protease variants described herein.

The following cassette mutagenesis method may be used to facilitate the construction of the protease variants of the present invention, although other methods may be used. First, the naturally-occurring gene encoding the protease is obtained and sequenced in whole or in part. Then the sequence is scanned for a point at which it is desired to make a mutation (deletion, insertion or substitution) of one or more amino acids in the encoded enzyme. The sequences flanking this point are evaluated for the presence of restriction sites for replacing a short segment of the gene with an oligonucleotide pool which when expressed will encode various mutants. Such restriction sites are preferably unique sites within the protease gene so as to facilitate the replacement of the gene segment. However, any convenient restriction site which is not overly redundant in the protease gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Once the naturally-occurring DNA or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

The variant proteases expressed upon transformation of the suitable hosts can be screened for enzymes isolated or recovered exhibiting desired characteristics, e.g. improved wash performance, substrate specificity, oxidation stability, pH-activity profiles and the like.

As used herein, proteolytic activity is defined as the rate of hydrolysis of peptide bonds per milligram of active enzyme. Many well known procedures exist for measuring proteolytic activity (K. M. Kalisz, "Microbial Proteinases," *Advances in Biochemical Engineering/Biotechnology*, A. Fiechter ed., 1988). Other exemplary methods for determining proteolytic activity include the various spectrophotometric assays measuring the conversion of selected substrates indirectly by measuring the change in absorption by the protease added to a predetermined concentration of substrate. Exemplary substrates include dimethyl casein, succinyl-Ala-Ala-Pro-Phe-pNA, and keratin (See U.S. patent Ser. No. 60/344,702).

In addition to or as an alternative to modified proteolytic activity, the variant enzymes of the present invention may have other modified properties such as $K_m$, $k_{cat}$, $k_{cat}/K_m$ ratio and/or modified substrate specificity and/or modified pH activity profile. These enzymes can be tailored for the particular substrate which is anticipated to be present, for example, in the preparation of peptides or for hydrolytic processes such as laundry uses.

A change in substrate specificity can be defined as a difference between the $k_{cat}/K_m$ ratio of the precursor enzyme and that of the mutant. The $k_{cat}/Km$ ratio is a measure of catalytic efficiency. Procaryotic carbonyl hydrolases with increased or diminished $k_{cat}/K_m$ ratios are described in the examples. Generally, the objective will be to secure a mutant having a greater (numerically larger) $k_{cat}/K_m$ ratio for a given substrate, thereby enabling the use of the enzyme to more efficiently act on a target substrate. An increase in $k_{cat}/K_m$ ratio for one substrate may be is accompanied by a reduction in $k_{cat}/K_m$ ratio for another substrate. This is a shift in substrate specificity, and mutants exhibiting such shifts have utility where the precursors are undesirable, e.g. to prevent undesired hydrolysis of a particular substrate in an admixture of substrates.

$k_{cat}$ and $K_m$ can be measured in accord with known procedures, or as described in Example 18 of U.S. Pat. No. 5,441,882.

Oxidation stability is a further objective which could be accomplished by protease variant described in the examples. The stability may be enhanced or diminished as is desired for various uses. Enhanced stability could be effected by deleting one or more methionine, tryptophan, cysteine or lysine residues and, optionally, substituting another amino acid residue not one of methionine, tryptophan, cysteine or lysine. The opposite substitutions result in diminished oxidation stability. The substituted residue could be alanyl, but neutral residues also are suitable.

Stability, for example thermostability, is a further objective which could be accomplished by the protease variant described in the examples. The stability may be enhanced or diminished as is desired for various uses. Enhanced stability could be effected by substitution one or more residues identified in the present application and, optionally, substituting another amino acid residue not one of the same. Thermostability is maintaining enzymatic acitivty over time at a given temperature. An improved thermostability involves the maintenance of a greater amount of enzymatic acitivity by the variant as compared to the precursor protease. For example, an increased level of enzymatic activity of the variant as compared to the precursor at a given temperature, typically the operation temperature of as measured.

Protease variants described herein could exhibit improved wash performance under specified wash conditions. For example, the protease variants could exhibit differing wash performance under different wash conditions, e.g. temperature, water hardness and/or detergent concentrations as indicated by the performance determined by various assays known in the art, e.g. WO 99/34011 ("An Improved Method of Assaying for a Preferred enzyme and/or Preferred Detergent composition.", published 8 Jul. 1999).

In the case of Bacillus subtilisin or its pre, prepro and pro forms, mutations at the earlier described positions produce mutants having changes in the characteristics described above or in the processing of the enzyme. Note that these amino acid position numbers are those assigned to B. amyloliquefaciens subtilisin as seen from FIG. 1. It should be understood that a deletion or insertion in the N-terminal direction from a given position will shift the relative amino acid positions so that a residue will not occupy its original or wild type numerical position. Also, allelic differences and the variation among various procaryotic species will result in positions shifts, so that position 169 in such subtilisins will not be occupied by glycine. In such cases the new positions for glycine will be considered equivalent to and embraced within the designation glycine+169. The new position for glycine+169 is readily identified by scanning the subtilisin in question for a region homologous to glycine+169 in FIG. 1.

One or more, ordinarily up to about 10, amino acid residues may be mutated. However, there is no limit to the number of mutations that are to be made aside from commercial practicality.

The enzymes herein may be obtained as salts. It is clear that the ionization state of a protein will be dependent on the pH of the surrounding medium, if it is in solution, or of the solution from which it is prepared, if it is in solid form. Acidic proteins are commonly prepared as, for example, the ammonium, sodium, or potassium salts; basic proteins as the chlorides, sulfates, or phosphates. Accordingly, the present application includes both electrically neutral and salt forms of the designated variant proteases, and the term protease refers to the organic structural backbone regardless of ionization state.

The protease variants are particularly useful in the food processing and cleaning arts. The carbonyl hydrolases, including protease variants and precursor proteases, are produced by fermentation as described herein and recovered by suitable techniques. See for example K. Anstrup, 1974, Industrial Aspects of Biochemistry, ed. B. Spencer pp. 23-46.

In one aspect of the invention, the objective is to secure a variant protease having altered, preferably improved wash performance as compared to a precursor protease in at least one detergent formulation and or under at least one set of wash conditions. They are formulated with detergents or other surfactants in accord with methods known per se for use in industrial processes, especially laundry. In the latter case the enzymes are combined with detergents, builders, bleach and/or fluorescent whitening agents as is known in the art for proteolytic enzymes. Suitable detergents include linear alkyl benzene sulfonates, alkyl ethoxylated sulfate, sulfated linear alcohol or ethoxylated linear alcohol. The compositions may be formulated in granular or liquid form. See for example U.S. Pat. Nos. 3,623,957; 4,404,128; 4,381,247; 4,404,115; 4,318,818; 4,261,868; 4,242,219; 4,142,999; 4,111,855; 4,011,169; 4,090,973; 3,985,686; 3,790,482; 3,749,671; 3,560,392; 3,558,498; and 3,557,002.

There is a variety of wash conditions including varying detergent formulations, wash water volume, wash water temperature and length of wash time that a protease variant might be exposed to. For example, detergent formulations used in different areas have different concentrations of their relevant components present in the wash water. For example, a European detergent typically has about 3000-8000 ppm of detergent components in the wash water while a Japanese detergent typically has less than 800, for example 667 ppm of detergent components in the wash water. In North America, particularly the United States, a detergent typically has about 800 to 2000 ppm, for example 975 ppm, of detergent components present in the wash water.

A low detergent concentration system includes detergents where less than about 800 ppm of detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of detergent components are present in the wash water. North American detergents are generally considered to be medium detergent concentration systems as they have approximately 975 ppm of detergent components present in the wash water. Brazil typically has approximately 1500 ppm of detergent components present in the wash water.

A high detergent concentration system includes detergents where greater than about 2000 ppm of detergent components are present in the wash water. European detergents are generally considered to be high detergent concentration systems as they have approximately 3000-8000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. As mentioned above, Brazil typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 800 ppm of detergent composition ("low detergent concentration geographies"), for example about 667 ppm in Japan, to between about 800 ppm to about 2000 ppm ("medium detergent concentration geographies"), for example about 975 ppm in U.S. and about 1500 ppm in Brazil, to greater than about 2000 ppm ("high detergent concentration geographies"), for example about 4500 ppm to about 5000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution about 62.79 of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature in European wash water is generally on the order of 30 to 50 degrees centigrade, typically about 40 degrees centigrade. The temperature in North American and/or Japanese wash water is generally less than European wash water, for example on the order of 10 to 30 degrees centigrade, typically about 20 degrees centigrade.

As a further example, different geographies use water hardness. Water hardness is typically described as grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million [parts per million converted to grains per U.S. gallon is ppm #divided by 17.1 equals grains per gallon] of hardness minerals.

| Water | Grains per gallon | Parts per million |
| --- | --- | --- |
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically 10-20 grains per gallon mixed $Ca^{2+}/Mg^{2+}$, for example about 15 grains per gallon mixed $Ca^{2+}/Mg^{2+}$. North American water hardness is typically greater than Japanese water hardness, but less than European water hardness, for example, between 3 to 10 grains, 3-8 grains or about 6 grains. Japanese water hardness is typically the lower than North American water hardness, typically less than 4, for example 3 grains per gallon mixed $Ca^{2+}/Mg^{2+}$.

Accordingly one aspect of the present invention includes a protease variant that shows improved wash performance in at least one set of wash conditions. Another aspect of the present invention includes a protease variant that shows improved wash performance in more than one wash conditions, e.g. in European, Japanese or North American conditions.

Based on the screening results obtained with the variant proteases, the noted mutations in *Bacillus* subtilisin are important to the proteolytic activity, performance and/or stability of these enzymes and the cleaning or wash performance of such variant enzymes.

Many of the protease variants of the invention are useful in formulating various detergent compositions or personal care formulations such as shampoos or lotions. A number of known compounds are suitable surfactants useful in compositions comprising the protease mutants of the invention. These include nonionic, anionic, cationic, or zwitterionic detergents, as disclosed in U.S. Pat. No. 4,404,128 to Barry J. Anderson and U.S. Pat. No. 4,261,868 to Jiri Flora, et al. A suitable detergent formulation is that described in Example 7 of U.S. Pat. No. 5,204,015 (previously incorporated by reference). The art is familiar with the different formulations which can be used as cleaning compositions. In addition to typical cleaning compositions, it is readily understood that the protease variants of the present invention may be used for any purpose that native or wild-type proteases are used. Thus, these variants can be used, for example, in bar or liquid soap applications, dishcare formulations, contact lens cleaning solutions or products, peptide hydrolysis, waste treatment, textile applications, as fusion-cleavage enzymes in protein production, etc. The variants of the present invention may comprise enhanced performance in a detergent composition (as compared to the precursor). As used herein, enhanced performance in a detergent is defined as increasing cleaning of certain enzyme sensitive stains such as grass or blood, as determined by usual evaluation after a standard wash cycle.

Proteases of the invention can be formulated into known powdered and liquid detergents having pH between 6.5 and 12.0 at levels of about 0.01 to about 5% (preferably 0.1% to 0.5%) by weight. These detergent cleaning compositions can also include other enzymes such as known proteases, amylases, cellulases, lipases or endoglycosidases, as well as builders and stabilizers.

The addition of proteases of the invention to conventional cleaning compositions does not create any special use limitation. In other words, any temperature and pH suitable for the detergent is also suitable for the present compositions as long as the pH is within the above range, and the temperature is below the described protease's denaturing temperature. In addition, proteases of the invention can be used in a cleaning composition without detergents, again either alone or in combination with builders and stabilizers.

The present invention also relates to cleaning compositions containing the protease variants of the invention. The cleaning compositions may additionally contain additives which are commonly used in cleaning compositions. These can be selected from, but not limited to, bleaches, surfactants, builders, enzymes and bleach catalysts. It would be readily apparent to one of ordinary skill in the art what additives are suitable for inclusion into the compositions. The list provided herein is by no means exhaustive and should be only taken as examples of suitable additives. It will also be readily apparent to one of ordinary skill in the art to only use those additives which are compatible with the enzymes and other components in the composition, for example, surfactant.

When present, the amount of additive present in the cleaning composition is from about 0.01% to about 99.9%, preferably about 1% to about 95%, more preferably about 1% to about 80%.

The variant proteases of the present invention can be included in animal feed such as part of animal feed additives as described in, for example, U.S. Pat. No. 5,612,055; U.S. Pat. No. 5,314,692; and U.S. Pat. No. 5,147,642.

One aspect of the invention is a composition for the treatment of a textile that includes variant proteases of the present invention. The composition can be used to treat for example silk or wool as described in publications such as RE 216,034; EP 134,267; U.S. Pat. No. 4,533,359; and EP 344,259.

The following is presented by way of example and is not to be construed as a limitation to the scope of the claims.

All publications and patents referenced herein are hereby incorporated by reference in their entirety.

EXAMPLE 1

A large number of protease variants can be produced and purified using methods well known in the art. Mutations can be made in *Bacillus* amyloliqefaciens (BPN') subtilisin or *Bacillus lentus* GG36 subtilisin. The variants can be selected from the following: K27A, K27C, K27E, K27Q, K27G, K27H, K271, K27L, K27M, K27F, K27P, K27S, K27T, K27W, K27Y, H39A, H39R, H39D, $H_{39}N$, $H_{39}C$, H39E, H39Q, H39G, H391, H39L, H39K, H39M, $H_{39}F$, H39P, H39T, H39W, H39Y, H39V, D41A, D41R, D41C, D41E, D41Q, D41G, D41H, D411, D41L, D41K, D41M, D41F, D41P, D41S, D41T, D41W, D41Y, D41V, R45A, R45D, R45N, R45C, R45E, R45Q, R45G, R45H, R451, R45L, R45K, R45M, R45F, R45P, R45S, R45T, R45W, R45Y, R45V, H67A, H67R, H67D, $H_{67}N$, $H_{67}C$, H67E, H67Q, H67G, H671, H67L, H67K, H67M, $H_{67}F$, H67P, H67S, H67T, H67W, H67Y, H67V, K94A, K94R, K94D, K94N, K94C, K94E, K94Q, K94G, K94H, K941, K94L, K94M, K94F, K94P, K94S, K94T, K94W, K94Y, K94V, E136A, E136D, E136N, E136C, E136G, E136H, E1361, E136L, E136K, E136M, E136F, E136P, E136S, E136T, E136W, E136Y, E136V, R170A, R170D, R170N, R170C, R170E, R170Q, R170G, R170H, R170I, R170L, R170K, R170M, R170F, R170P, R170S, R170T, R170W, R170Y, R170V, D181A, D181R, D181N, D181C, D181E, D181Q, D181G, D181H, D181, D181L, D181K, D181M, D181F, D181P, D181S, D181T, D181W, D181Y, D181V, D197A, D197R, D197N, D197C, D197E, D197Q, D197G, D197H, D197I, D197L, D197K, D197M, D197F, D197P, D197S, D197T, D197W, D197Y, D197V, R247A, R247D, R247N, R247C, R247E, R247Q, R247G, R247H, R2471, R247L, R247K, R247M, R247F, R247P, R247S, R247T, R247W, R247Y, R247V, H249A, H249R, H249D, H249N, H249C, H249E, H249Q, H249G, H2491, H249K, H249M, H249F, H249P, H249S, H249T, H249W, H249V, K251A, K251D, K251C, K251Q, K251G, K251H, K251I, K251L, K251M, K251F, K251P, K251S, K251T, K251W, K251Y, K251V, E271A, E271R, E271D, E271N, E271C, E271H, E271I, E271L, E271K, E271M, E271F, E271P, E271S, E271T, E271W, E271Y, and/or E271V of *Bacillus amyloliquefaciens* (SEQ ID No:3).

EXAMPLE 2

A large number of protease variants can be produced and purified using methods well known in the art. Mutations can be made in *Bacillus* amyloliqefaciens (BPN') subtilisin (SEQ ID No:3) or *Bacillus lentus* GG36 subtilisin (SEQ ID No:6). The variants can be made with insertions, deletions or substitutions at the amino acids equivalent to those at positions: 5, 7, 23, 26, 28-31, 34, 47, 63, 65, 66, 69, 70, 73, 82-85, 88, 90, 92, 93, 105, 113, 125, 138, 139,148-151, 176, 178, 179, 193, 196, 200, 201, 202, 207, 219, 220, 223, 229, 233, 250, 266, 267 and 273 of *Bacillus amyloliquefaciens* (BPN') (SEQ ID No:3).

EXAMPLE 3

A large number of the protease variants produced in Examples 1 and/or 2 can be tested for performance in two types of detergent and wash conditions using a microswatch assay described in "An improved method of assaying for a preferred enzyme and/or preferred detergent composition", U.S. Ser. No. 60/068,796.

The variant proteases can be assayed and tested various detergents. For example, a possible detergent can be 0.67 g/l filtered Ariel Ultra (Procter & Gamble, Cincinnati, Ohio, USA), in a solution containing 3 grains per gallon mixed $Ca^{2+}/Mg^{2+}$ hardness, and 0.3 ppm enzyme used in each well at 20° C. Another exemplary detergent can be 3.38 g/l filtered Ariel Futur (Procter & Gamble, Cincinnati, Ohio, USA), in a solution containing 15 grains per gallon mixed $Ca^{2+}/Mg^{2+}$ hardness, and 0.3 ppm enzyme used in each well at 40° C. A higher relative value as compared to the wild-type could indicate and improve detergent efficacy.

EXAMPLE 4

The variant proteases which can be assayed as described in Examples 1 & 2 can also be assayed in other different detergents. The same performance tests as in Example 2 can be done on the noted variant proteases with the following detergents: a first detergent can be 0.67 g/l filtered Ariel Ultra (Procter & Gamble, Cincinnati, Ohio, USA), in a solution containing 3 grains per gallon mixed $Ca^{2+}/Mg^{2+}$ hardness, and 0.3 ppm enzyme could be used in each well at 20° C. A second detergent can be 3.38 g/l filtered Ariel Futur (Procter & Gamble, Cincinnati, Ohio, USA), in a solution containing 15 grains per gallon mixed $Ca^{2+}/Mg^{2+}$ hardness, and 0.3 ppm enzyme can be used in each well at 40° C. A third detergent can be 3.5 g/l HSP1 detergent (Procter & Gamble, Cincinnati, Ohio, USA), in a solution containing 8 grains per gallon mixed $Ca^{2+}/Mg^{2+}$ hardness, and 0.3 ppm enzyme can be used in each well at 20° C. A fourth detergent can be 1.5 ml/l Tide KT detergent (Procter & Gamble, Cincinnati, Ohio, USA), in a solution containing 3 grains per gallon mixed $Ca^{2+}/Mg^{2+}$ hardness, and 0.3 ppm enzyme can be used in each well at 20° C.

EXAMPLE 5

A large number of protease variants were produced and purified using methods well known in the art. All mutations were made in Bacillus lentus GG36 subtilisin. The variants are shown in Table 3.

To construct the GG36 site saturated libraries and site specific variants, three PCR reactions were performed: two PCR's to introduce the mutated codon of interest in GG36 and a fusion PCR to construct the expression vector including the desired mutation(s).

The GG36 codons of interest are numbered according to the BPN' numbering (listed in FIGS. 1A-C and 3A-B).

For the site saturated library construction:

The method of mutagenesis was based on the region-specific mutation approach (Teplyakov et al., 1992) in which the creation of all possible mutations at a time in a specific DNA codon was performed using a forward and reversed complimentary oligonucleotide primer set with a length of 30-40 nucleotides enclosing a specific designed triple DNA sequence NNS ((A,C,T or G), (A,C,T or G), (C or G)) that correspond with the sequence of the codon to be mutated and guarantees randomly incorporation of nucleotides at that codon.

For the site specific variant construction:

The forward and reverse mutagenic primer enclose the three desired mutation(s) in the middle of the primer with ~15 bases of homologues sequence on both sides. These mutation(s), which cover the codon of interest, are specific for the desired amino acid and are synthesized by design.

The second primer set used to construct the libraries and variants contains the pVS08 ApaI digestion site together with its flanking nucleotide sequence.

ApaI Primers:

```
                                         (SEQ ID NO:7)
Forward ApaI primer:  GTGTGTGGGCCCATCAGTCTGACGACC (SEQ ID NO:8)
Reverse ApaI primer:  GTGTGTGGGCCCTATTCGGATATTGAG
```

The introduction of the mutation(s) in GG36 molecules was performed using Invitrogen Platinum® Taq DNA Polymerase High Fidelity (Carlsbad, Calif., Cat. no. 11304-102) together with pVS08 template DNA and Forward mutagenic is primer and Reverse ApaI primer for reaction 1, or Reverse mutagenic primer and Forward ApaI primer for reaction 2.

The construction of the expression vector including the desired mutation(s) was accomplished by a fusion PCR using PCR fragment of both reaction 1 and 2, forward and reverse ApaI primer and Invitrogen Platinum® Taq DNA Polymerase High Fidelity (Cat. no. 11304-102).

All PCR's were executed according to Invitrogen protocol supplied with the polymerases, except for the number of cycles: 20 instead of 30. Two separate PCR reactions are performed using Invitrogen Platinum® Taq DNA Polymerase High Fidelity (Cat. no.11304-102): the amplified linear 5.6 Kb fragment was purified (using Qiagen® Qiaquick PCR purification kit Cat. no. 28106) and digested with ApaI restriction enzyme to create cohesive ends on both sides of the fusion fragment:

35 µL purified DNA fragment
4 µL React® 4 buffer (Invitrogen®: 20 mM Tris-HCl, 5 mM $MgCl_2$, 50 mM KCl, pH 7.4)
1 µL ApaI, 10 units/ml (Invitrogen® Cat. no. 15440-019)

Reaction conditions: 1 hour, 30° C.

An additional digestion with Invitrogen DpnI was performed to remove the pVS08 template DNA:
40 µL ApaI digested DNA fragment
1 µL DpnI, 4 units/µL (Invitrogen® Cat. no. 15242-019)

Reaction conditions: 16-20 hours, 37° C.

Ligation of the double digested and purified fragment results in new circular DNA containing the desired mutation with was directly transformed to competent Bacillus subtilis:

30 µL of purified ApaI and DpnI digested DNA fragment
8 µL T4 DNA Ligase buffer (Invitrogen® Cat. no. 46300-018)
1 µL T4 DNA Ligase, 1 unit/µL (Invitrogen® Cat. no. 15224-017)

Reaction conditions: 16-20 hours, 16° C.

Ligation mixtures were transformed to Bacillus subtilis BG2864 (Naki et al., 1997) using the method of Anagnostopoulos and Spizizen (1961) and selected for chloramphenicol resistance and protease activity.

Method for Protein Production

Inoculate 1-50 µL of glycerol culture in Mops media (Frederick C. Neidhardt et al., 1974) containing carbon source (Glucose and Maltodextrine, 10.5 and 17.5 g/l) a nitrogen source (Urea, 3.6 g/l), and essential nutrients such as phosphate (0.5 g/l) and sulphate (0.5 g/l) and further supplemented with trace elements (Fe, Mn, Zn, Cu, Co, 1-4 mg/ml). The medium was buffered with a MOPS/Tricine mixture resulting in a pH varying 7 to 8. Incubate the culture for 1-5 days at 37° C./220 rpm (Infors HT® Multitron II).

REFERENCES

Protein engineering of the high-alkaline serine protease PB92 from Bacillus alcalophilus: functional and structural consequences of mutation at the S4 substrate binding pocket.
Teplyakov A V, van der Laan J M, Lammers M, Kelders H, Kalk K H, Misset O, Mulleners L J, Dijkstra B W. Protein Eng. 1992 July;5(5):413-20.

Selection of a subtilisin-hyper producing Bacillus in a highly structured environment by D. Naki, C. Paech, G. Ganshaw, V. Schellenberger in Appl Microbiol Biotechnol (1998) 49:290-294

Requirements for transformation in Bacillus subtilis by Anagnostopoulos, C. and Spizizen, J. in J. Bacteriol. 81, 741-746 (1961).

Culture Medium for Enterobacteria by Frederick C. Neidhardt, Philip L. Bloch and David F. Smith in Journal of Bacteriology, September 1974. p736-747 Vol. 119. No. 3.

TABLE 3

| GG36 | | |
|---|---|---|
| R45N | G118E | E27IR |
| R45N | P14R | |
| R45N | N204R | |

TABLE 3-continued

| | |
|---|---|
| D181N | G118D |
| R45N | G258R |
| R170S | N204R |
| R45N | S216R |
| R170S | P14R |
| R170S | G61R |
| R170S | S49R |
| R170S | S216R |
| R170S | S128R |
| R170S | G258R |
| R170S | A1R |
| R170S | G100R |
| R45N | S128R |
| R45N | G61R |
| R45N | A1R |
| D181N | G258D |
| E271T | S49E |
| E271T | T66E |
| E271T | G102E |
| E271T | G100E |
| E271T | S128E |
| K27T | G100E |
| K251G | S87K |

EXAMPLE 6

A large number of the protease variants produced in Example 1 were tested for performance in two types of detergent and wash conditions using a microswatch assay described in "An improved method of assaying for a preferred enzyme and/or preferred detergent composition", U.S. Ser. No. 09/554,992 [WO 99/34011].

Table 4 lists the variant proteases assayed and the results of testing in two different detergents. For column A and C, the assayed material was produced by growing the transformant strains in a MTP [what do these initials stand for?] plate according to [citation?]. For columns B and D, the assayed material was produced by growing the transformant strains in a shake flask (250 ml) according to [citation?]. For columns A and B, the detergent was 7.6 g/l filtered Ariel Regular (Procter & Gamble, Cincinnati, Ohio, USA), in a solution containing 15 grains per gallon mixed $Ca^{2+}/Mg^{2+}$ hardness, and 0.5 ppm enzyme was used in each well at 40° C. [European conditions]. For columns C and D, the detergent was 0.67 g/l filtered Tide Opal (Procter & Gamble, Cincinnati, Ohio, USA), in a solution containing 3 grains per gallon mixed $Ca^{2+}/Mg^{2+}$ hardness, and 0.5 ppm enzyme was used in each well at 20° C. [Japanese conditions]. A performance index was calculated by the following formula:

Cleaning performance of the variant divided by cleaning performance of GG36 (wild-type)

Four performance values were averaged to arrive at the values shown in Table 4.

TABLE 4

| | |
|---|---|
| GG36 | 1.00 |
| R170S-A1R | 2.09 |
| R170S-G61R | 2.03 |
| R170S-N204R | 1.79 |
| R45N-G118E-E271R | 1.75 |
| D181N-G118D | 1.54 |
| R45N-N204R | 1.47 |
| K251G-S87K | 1.39 |
| R45N-P14R | 1.28 |
| R45N-G258R | 1.23 |
| R170S-S216R | 1.21 |
| R45N-S216R | 1.05 |

TABLE 4-continued

| | |
|---|---|
| R170S-P14R | 1.03 |
| R45N-A1R | 1.01 |
| R170S-S49R | 0.93 |
| R45N-G61R | 0.87 |
| D181N-G258D | 0.81 |
| R45N-S128R | 0.80 |
| R170S-S128R | 0.63 |
| R170S-G258R | 0.36 |
| E271T-S49E | 0.34 |
| E271T-G100E | * |
| E271T-T66E | * |
| E271T-G102E | * |
| R170S-G100R | * |
| E271T-S128E | * |
| K27T-G100E | * |

* too low protease level for reliable performance test

TABLE 5

| variant | Performance index |
|---|---|
| GG36 | 1.00 |
| E271T-G100E | 3.22 |
| E271T-S128E | 2.33 |
| K251G-S87K | 2.06 |
| K27T-G100E | 2.04 |
| E271T-G102E | 1.85 |
| R170S-G100R | 1.79 |
| R170S-A1R | 1.55 |
| E271T-S49E | 1.43 |
| R170S-S128R | 0.85 |
| R170S-S49R | 0.80 |
| R170S-N204R | 0.77 |
| R170S-P14R | 0.76 |
| R45N-A1R | 0.75 |
| R170S-G61R | 0.67 |
| R170S-S216R | 0.61 |
| R45N-P14R | 0.53 |
| R45N-G258R | 0.53 |
| R170S-G258R | 0.45 |
| R45N-G61R | 0.43 |
| R45N-S216R | 0.32 |
| R45N-N204R | 0.31 |
| D181N-G258D | 0.28 |
| D181N-G118D | 0.28 |
| R45N-G118E-E271R | 0.25 |
| R45N-S128R | 0.22 |
| E271T-T66E | * |

* too low protease level for reliable performance test
[1]GG 36 is the wild type protease of *Bacillus lentus* (SEQ ID NO. 4)

As a result of the above described assays, some variants exhibited a performance index greater than that of the GG36 wild type protease. For example, the variants R45N-G118E-E271R, R45N-P14R, R45N-N204R, D181N-G118D and R45N-G258R exhibited performance indices of 1.75, 1.28, 1.28, 1.24 and 1.23 respectively (Table 4), in a microswatch assay (WO 99/34011) under European conditions (15 grains per gallon mixed $Ca^{2+}/Mg^{2+}$ hardness, 40 degrees Centigrade, 0.5 ppm). The variants R170S-A1P, R170S-G61R, R170S-N204R, K251G-S87K, and R170S-S216R exhibited performance indices of 2.09, 2.03, 1.79, 1.54, 1.47, 1.39, and 1.21 respectively (Table 5). The variants E271T-G100E, E271T-G102E, E271T-S128E, K27T-G100E, R170S-G100R, and E271T-S49E exhibited performance indices of 3.22, 1.85, 2.33, 2.04, 1.79 and 1.43 respectively (Column Table 5), in the Microswatch 96 microtiter well plate (WO 99/34011) assay under Japanese conditions (3 grains per gallon mixed $Ca^{2+}/Mg^{2+}$ hardness, 20 degrees centigrade, 0.5 ppm). The variants K251G-S87K, R170S-A1R, and E271T-S128E exhibited performance indices of 2.06, 1.55 and 1.20 respectively (Table 5). Variants K251 G-S87K and R170S-A1R exhibited performance indices of greater than 1.00 under both Japanese and European conditions.

Although the present invention has been discussed and exemplified in connection with various specific embodiments thereof, this is not to be construed as a limitation to the applicability and scope of the disclosure, which extends to all combinations and subcombinations of features mentioned and described in the foregoing as well as the attached claims.

The invention claimed is:

1. A subtilisin variant of a precursor subtilisin wherein the subtilisin variant has the same net electrostatic charge at pH 6.0 as the net electrostatic charge of the precursor subtilisin at pH 6.0 and comprises the amino acid substitution R170S, and further comprises one or more amino acid substitutions selected from the group consisting of R45N, K251G and E271T, wherein the positions are numbered by correspondence with the amino acid sequence of *Bacillus amyloliquefaciens* subtilisin set forth in SEQ ID NO:3, the subtilisin variant has proteolytic activity, and is a mature subtilisin comprising the gaps present in the amino acid sequence of a *Bacillus lentus* subtilisin relative to the amino acid seguence of the *Bacillus amyloliguefaciens* subtilisin depicted in FIG. 3.

2. The subtilisin variant of claim 1, further comprising one or more additional amino acid substitutions at positions corresponding to positions 14, 49, 102, and 258 of the amino acid seguence of the *Bacillus amyloliquefaciens* subtilisin set forth in SEQ ID NO:3.

3. The subtilisin variant of claim 2 wherein said subtilisin variant is selected from the group consisting of S49R+G102E+R170S+E271T and P14R+R45N+R170S+G258R.

4. A DNA encoding the subtilisin variant of claim 1.

5. An expression vector comprising the DNA of claim 4.

6. A host cell comprising the expression vector of claim 5.

7. A cleaning composition comprising the subtilisin variant of claim 1 and a surfactant.

* * * * *

SEQUENCE LISTING

<160> NUMBER OF SEQ ID NOS: 10

<210> SEQ ID NO 1
<211> LENGTH: 1494
<212> TYPE: DNA
<213> ORGANISM: Bacillus amyloliquefaciens

<400> SEQUENCE: 1

```
ggtctactaa aatattattc catactatac aattaataca cagaataatc tgtctattgg      60
ttattctgca aatgaaaaaa aggagaggat aaagagtgag aggcaaaaaa gtatggatca     120
gtttgctgtt tgctttagcg ttaatctta cgatggcgtt cggcagcaca tcctctgccc     180
aggcggcagg gaaatcaaac ggggaaaaga aatatattgt cgggtttaaa cagacaatga    240
gcacgatgag cgccgctaag aagaaagatg tcatttctga aaaaggcggg aaagtgcaaa    300
agcaattcaa atatgtagac gcagcttcag ctacattaaa cgaaaaagct gtaaaagaat    360
tgaaaaaaga cccgagcgtc gcttacgttg aagaagatca cgtagcacat gcgtacgcgc    420
agtccgtgcc ttacggcgta tcacaaatta aagcccctgc tctgcactct caaggctaca    480
ctggatcaaa tgttaaagta gcggttatcg acagcggtat cgattcttct catcctgatt    540
taaaggtagc aggcggagcc agcatggttc cttctgaaac aaatcctttc caagacaaca    600
actctcacgg aactcacgtt gccggcacag ttgcggctct taataactca atcggtgtat    660
taggcgttgc gccaagcgca tcactttacg ctgtaaaagt tctcggtgct gacggttccg    720
gccaatacag ctggatcatt aacggaatcg agtgggcgat cgcaaacaat atggacgtta    780
ttaacatgag cctcggcgga ccttctggtt ctgctgcttt aaaagcggca gttgataaag    840
ccgttgcatc cggcgtcgta gtcgttgcgg cagccggtaa cgaaggcact tccggcagct    900
caagcacagt gggctaccct ggtaaatacc cttctgtcat tgcagtaggc gctgttgaca    960
gcagcaacca aagagcatct ttctcaagcg taggacctga gcttgatgtc atggcacctg   1020
gcgtatctat ccaaagcacg cttcctggaa acaaatacgg ggcgtacaac ggtacgtcaa   1080
tggcatctcc gcacgttgcc ggagcggctg ctttgattct ttctaagcac ccgaactgga   1140
caaacactca agtccgcagc agtttagaaa acaccactac aaaacttggt gattctttct   1200
actatggaaa agggctgatc aacgtacagg cggcagctca gtaaaacata aaaaccggc   1260
cttggccccg ccggtttttt attttctc ctccgcatgt tcaatccgct ccataatcga   1320
cggatggctc cctctgaaaa ttttaacgag aaacggcggg ttgacccggc tcagtcccgt   1380
aacggccaag tcctgaaacg tctcaatcgc cgcttcccgg tttccggtca gctcaatgcc   1440
gtaacggtcg gcggcgtttt cctgataccg ggagacggca ttcgtaatcg gatc          1494
```

<210> SEQ ID NO 2
<211> LENGTH: 382
<212> TYPE: PRT
<213> ORGANISM: Bacillus amyloliquefaciens
<220> FEATURE:
<221> NAME/KEY: VARIANT
<222> LOCATION: 163, 164
<223> OTHER INFORMATION: Xaa = Pro or Asn
<220> FEATURE:

```
<221> NAME/KEY: VARIANT
<222> LOCATION: 168
<223> OTHER INFORMATION: Xaa = Asp or Asn
<220> FEATURE:
<221> NAME/KEY: VARIANT
<222> LOCATION: 195, 196
<223> OTHER INFORMATION: Xaa = Ser or Ala
<220> FEATURE:
<221> NAME/KEY: VARIANT
<222> LOCATION: 205, 206
<223> OTHER INFORMATION: Xaa = Asp or Ala
<220> FEATURE:
<221> NAME/KEY: VARIANT
<222> LOCATION: 265, 266
<223> OTHER INFORMATION: Xaa = Ser or Thr
<220> FEATURE:
<221> NAME/KEY: VARIANT
<222> LOCATION: 358
<223> OTHER INFORMATION: Xaa = Glu or Gln

<400> SEQUENCE: 2

Met Arg Gly Lys Lys Val Trp Ile Ser Leu Leu Phe Ala Leu Ala Leu
 1               5                   10                  15

Ile Phe Thr Met Ala Phe Gly Ser Thr Ser Ser Ala Gly Ala Ala Gly
            20                  25                  30

Lys Ser Asn Gly Glu Lys Lys Tyr Ile Val Gly Phe Lys Gln Thr Met
        35                  40                  45

Ser Thr Met Ser Ala Ala Lys Lys Lys Asp Val Ile Ser Glu Lys Gly
 50                  55                  60

Gly Lys Val Gln Lys Gln Phe Lys Tyr Val Asp Ala Ala Ser Ala Thr
65                  70                  75                  80

Leu Asn Glu Lys Ala Val Lys Glu Leu Lys Lys Asp Pro Ser Val Ala
                85                  90                  95

Tyr Val Glu Glu Asp His Val Ala His Ala Tyr Ala Gln Ser Val Pro
            100                 105                 110

Tyr Gly Val Ser Gln Ile Lys Ala Pro Ala Leu His Ser Gln Gly Tyr
        115                 120                 125

Thr Gly Ser Asn Val Lys Val Ala Val Ile Asp Ser Gly Ile Asp Ser
130                 135                 140

Ser His Pro Asp Leu Lys Val Ala Gly Gly Ala Ser Met Val Pro Ser
145                 150                 155                 160

Glu Thr Xaa Xaa Phe Gln Asp Xaa Asn Ser His Gly Thr His Val Ala
                165                 170                 175

Gly Thr Val Ala Ala Leu Asn Asn Ser Ile Gly Val Leu Gly Val Ala
            180                 185                 190

Pro Ser Xaa Xaa Leu Tyr Ala Val Lys Val Leu Gly Xaa Xaa Gly Ser
        195                 200                 205

Gly Gln Tyr Ser Trp Ile Ile Asn Gly Ile Glu Trp Ala Ile Ala Asn
    210                 215                 220

Asn Met Asp Val Ile Asn Met Ser Leu Gly Gly Pro Ser Gly Ser Ala
225                 230                 235                 240

Ala Leu Lys Ala Ala Val Asp Lys Ala Val Ala Ser Gly Val Val Val
                245                 250                 255

Val Ala Ala Ala Gly Asn Glu Gly Xaa Xaa Gly Ser Ser Ser Thr Val
            260                 265                 270

Gly Tyr Pro Gly Lys Tyr Pro Ser Val Ile Ala Val Gly Ala Val Asp
        275                 280                 285

Ser Ser Asn Gln Arg Ala Ser Phe Ser Ser Val Gly Pro Glu Leu Asp
290                 295                 300
```

-continued

```
Val Met Ala Pro Gly Val Ser Ile Gln Ser Thr Leu Pro Gly Asn Lys
305                 310                 315                 320

Tyr Gly Ala Tyr Asn Gly Thr Ser Met Ala Ser Pro His Val Ala Gly
            325                 330                 335

Ala Ala Ala Leu Ile Leu Ser Lys His Pro Asn Trp Thr Asn Thr Gln
        340                 345                 350

Val Arg Ser Ser Leu Xaa Asn Thr Thr Thr Lys Leu Gly Asp Ser Phe
    355                 360                 365

Tyr Tyr Gly Lys Gly Leu Ile Asn Val Gln Ala Ala Gln
370                 375                 380
```

<210> SEQ ID NO 3
<211> LENGTH: 275
<212> TYPE: PRT
<213> ORGANISM: Bacillus amyloliquefaciens

<400> SEQUENCE: 3

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
130                 135                 140

Ser Gly Val Val Val Ala Ala Ala Gly Asn Glu Gly Thr Ser Gly Ser
145                 150                 155                 160

Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```

<210> SEQ ID NO 4

```
<211> LENGTH: 275
<212> TYPE: PRT
<213> ORGANISM: Bacillus subtilis

<400> SEQUENCE: 4

Ala Gln Ser Val Pro Tyr Gly Ile Ser Gln Ile Lys Ala Pro Ala Leu
 1               5                  10                  15

His Ser Gln Gly Tyr Thr Gly Ser Asn Val Lys Val Ala Val Ile Asp
                20                  25                  30

Ser Gly Ile Asp Ser Ser His Pro Asp Leu Asn Val Arg Gly Gly Ala
            35                  40                  45

Ser Phe Val Pro Ser Glu Thr Asn Pro Tyr Gln Asp Gly Ser Ser His
 50                  55                  60

Gly Thr His Val Ala Gly Thr Ile Ala Ala Leu Asn Asn Ser Ile Gly
 65                  70                  75                  80

Val Leu Gly Val Ser Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
                100                 105                 110

Trp Ala Ile Ser Asn Asn Met Asp Val Ile Asn Met Ser Leu Gly Gly
            115                 120                 125

Pro Thr Gly Ser Thr Ala Leu Lys Thr Val Val Asp Lys Ala Val Ser
130                 135                 140

Ser Gly Ile Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
                180                 185                 190

Gly Ser Glu Leu Asp Val Met Ala Pro Gly Val Ser Ile Gln Ser Thr
            195                 200                 205

Leu Pro Gly Gly Thr Tyr Gly Ala Tyr Asn Gly Thr Ser Met Ala Thr
210                 215                 220

Pro His Val Ala Gly Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Asn Ser Phe Tyr Tyr Gly Lys Gly Leu Ile Asn Val Gln Ala
                260                 265                 270

Ala Ala Gln
        275

<210> SEQ ID NO 5
<211> LENGTH: 274
<212> TYPE: PRT
<213> ORGANISM: Bacillus licheniformis

<400> SEQUENCE: 5

Ala Gln Thr Val Pro Tyr Gly Ile Pro Leu Ile Lys Ala Asp Lys Val
 1               5                  10                  15

Gln Ala Gln Gly Phe Lys Gly Ala Asn Val Lys Val Ala Val Leu Asp
                20                  25                  30

Thr Gly Ile Gln Ala Ser His Pro Asp Leu Asn Val Val Gly Gly Ala
            35                  40                  45

Ser Phe Val Ala Gly Glu Ala Tyr Asn Thr Asp Gly Asn Gly His Gly
 50                  55                  60
```

```
Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
            115                 120                 125

Ser Gly Ser Thr Ala Met Lys Gln Ala Val Asp Asn Ala Tyr Ala Arg
            130                 135                 140

Gly Val Val Val Ala Ala Ala Gly Asn Ser Gly Asn Ser Gly Ser
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
            195                 200                 205

Pro Thr Asn Thr Tyr Ala Thr Leu Asn Gly Thr Ser Met Ala Ser Pro
210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
                260                 265                 270

Ala Gln

<210> SEQ ID NO 6
<211> LENGTH: 269
<212> TYPE: PRT
<213> ORGANISM: Bacillus lentus

<400> SEQUENCE: 6

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Gly Ser Ile Ser
145                 150                 155                 160
```

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

<210> SEQ ID NO 7
<211> LENGTH: 27
<212> TYPE: DNA
<213> ORGANISM: Artificial Sequence
<220> FEATURE:
<223> OTHER INFORMATION: primer

<400> SEQUENCE: 7
gtgtgtgggc ccatcagtct gacgacc                                    27

<210> SEQ ID NO 8
<211> LENGTH: 27
<212> TYPE: DNA
<213> ORGANISM: Artificial Sequence
<220> FEATURE:
<223> OTHER INFORMATION: primer

<400> SEQUENCE: 8
gtgtgtgggc cctattcgga tattgag                                    27

<210> SEQ ID NO 9
<211> LENGTH: 275
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(275)
<223> OTHER INFORMATION: Xaa = Any Amino Acid

<400> SEQUENCE: 9

Ala Gln Ser Val Pro Xaa Gly Xaa Xaa Xaa Xaa Xaa Ala Pro Ala Xaa
1               5                   10                  15

His Xaa Xaa Gly Xaa Thr Gly Ser Xaa Val Lys Val Ala Val Xaa Asp
            20                  25                  30

Xaa Gly Xaa Xaa Xaa Xaa His Pro Asp Leu Xaa Xaa Xaa Gly Gly Ala
        35                  40                  45

Ser Xaa Val Pro Xaa Xaa Xaa Xaa Xaa Gln Asp Xaa Asn Xaa His
    50                  55                  60

Gly Thr His Val Ala Gly Thr Xaa Ala Ala Leu Asn Asn Ser Ile Gly
65                  70                  75                  80

Val Leu Gly Val Ala Pro Ser Ala Xaa Leu Tyr Ala Val Lys Val Leu
                85                  90                  95

Gly Ala Xaa Gly Ser Gly Xaa Xaa Ser Xaa Leu Xaa Xaa Gly Xaa Glu

```
                   100                 105                 110
Trp Ala Xaa Asn Xaa Xaa Xaa Val Xaa Asn Xaa Ser Leu Gly Xaa
            115                 120                 125

Pro Ser Xaa Ser Xaa Xaa Xaa Xaa Ala Xaa Xaa Xaa Xaa Xaa
        130                 135                 140

Xaa Gly Val Xaa Val Val Ala Ala Xaa Gly Asn Xaa Gly Xaa Xaa
145                 150                 155                 160

Xaa Xaa Xaa Xaa Xaa Xaa Tyr Pro Xaa Xaa Tyr Xaa Xaa Xaa Ala
                165                 170                 175

Val Gly Ala Xaa Asp Xaa Xaa Asn Xaa Xaa Ala Ser Phe Ser Xaa Xaa
            180                 185                 190

Gly Xaa Xaa Leu Asp Xaa Xaa Ala Pro Gly Val Xaa Xaa Gln Ser Thr
        195                 200                 205

Xaa Pro Gly Xaa Xaa Tyr Xaa Xaa Xaa Asn Gly Thr Ser Met Ala Xaa
        210                 215                 220

Pro His Val Ala Gly Ala Ala Leu Xaa Xaa Xaa Lys Xaa Xaa Xaa
225                 230                 235                 240

Trp Xaa Xaa Xaa Gln Xaa Arg Xaa Xaa Leu Xaa Asn Thr Xaa Xaa Xaa
                245                 250                 255

Leu Gly Xaa Xaa Xaa Xaa Tyr Gly Xaa Gly Leu Xaa Asn Xaa Xaa Ala
            260                 265                 270

Ala Xaa Xaa
        275

<210> SEQ ID NO 10
<211> LENGTH: 4
<212> TYPE: PRT
<213> ORGANISM: Artificial Sequence
<220> FEATURE:
<223> OTHER INFORMATION: assay protein

<400> SEQUENCE: 10

Ala Ala Pro Phe
1
```